United States Patent
Yap et al.

(10) Patent No.: US 9,841,014 B2
(45) Date of Patent: Dec. 12, 2017

(54) INSULIN PUMP DATA ACQUISITION DEVICE AND SYSTEM

(71) Applicant: MEDTRONIC MINIMED, INC., Northridge, CA (US)

(72) Inventors: Darren Y. K. Yap, Valencia, CA (US); Carl A. Link, Westlake Village, CA (US); Vincent Ming Hai Chow, Daly City, CA (US); William Jackson Dannemann, New Canaan, CT (US); Jennifer Marie Reitmajer, Granada Hills, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 183 days.

(21) Appl. No.: 14/708,561

(22) Filed: May 11, 2015

(65) Prior Publication Data
US 2016/0106911 A1 Apr. 21, 2016

Related U.S. Application Data

(63) Continuation-in-part of application No. 14/518,878, filed on Oct. 20, 2014.

(51) Int. Cl.
| | |
|---|---|
| *G01N 17/00* | (2006.01) |
| *G01N 33/00* | (2006.01) |
| *F04B 51/00* | (2006.01) |
| *F04B 49/06* | (2006.01) |
| *A61M 5/14* | (2006.01) |

(52) U.S. Cl.
CPC ............ *F04B 51/00* (2013.01); *F04B 49/065* (2013.01); *A61M 5/14* (2013.01); *A61M 2205/33* (2013.01); *A61M 2205/3327* (2013.01); *A61M 2205/3368* (2013.01); *A61M 2205/52* (2013.01); *A61M 2205/8206* (2013.01); *A61M 2209/02* (2013.01)

(58) Field of Classification Search
USPC .................... 73/865.8; 702/183; 600/301
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |

(Continued)

*Primary Examiner* — Clayton E Laballe
*Assistant Examiner* — Warren K Fenwick
(74) *Attorney, Agent, or Firm* — Medtronic MiniMed, Inc.

(57) ABSTRACT

An insulin pump data acquisition device & system including: an insulin pump data acquisition device for use with an insulin pump, the data acquisition device including a holster having a wall defining an interior volume and an exterior volume, the exterior volume being sized to removably secure the insulin pump; an environmental sensor operable to generate environmental data in response to environmental conditions; memory operably connected to the environmental sensor, the memory being operable to store the environmental data; a controller operably connected to the environmental sensor and the memory, the controller being operable to control reading of the environmental data from the environmental sensor and writing of the environmental data to the memory; and a battery operably connected to power the environmental sensor, the memory, and the controller. The environmental sensor, the memory, the controller, and the battery are disposed within the interior volume.

17 Claims, 20 Drawing Sheets

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 * | 5/2011 | Moberg ............... A61M 5/142 604/65 |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 8,181,849 | B2 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 2003/0055406 | A1 * | 3/2003 | Lebel ............... A61N 1/37211 604/891.1 |
| 2007/0123819 | A1 | 5/2007 | Mernoe et al. |
| 2007/0258894 | A1 * | 11/2007 | Melker ............... A61B 5/145 424/9.1 |
| 2008/0119705 | A1 * | 5/2008 | Patel ............... G06F 19/3412 600/347 |
| 2010/0160861 | A1 | 6/2010 | Causey, III et al. |
| 2010/0174239 | A1 * | 7/2010 | Yodfat ............... A61M 5/14232 604/153 |
| 2012/0053428 | A1 * | 3/2012 | Bernstein ........... A61B 5/14532 600/301 |
| 2013/0198685 | A1 * | 8/2013 | Bernini ............... G06F 3/0484 715/800 |
| 2013/0298063 | A1 * | 11/2013 | Joy ............... A61B 5/14532 715/771 |
| 2013/0345664 | A1 * | 12/2013 | Beck ............... A61M 5/1723 604/504 |
| 2014/0128834 | A1 * | 5/2014 | Thomson ........... A61M 5/1723 604/500 |
| 2015/0100013 | A1 * | 4/2015 | Uchiyama ......... A61M 5/14228 604/67 |
| 2015/0209114 | A1 * | 7/2015 | Burkholz ............ A61M 5/142 600/562 |
| 2016/0106910 | A1 * | 4/2016 | Yap ............... A61M 5/14244 73/865.8 |

\* cited by examiner

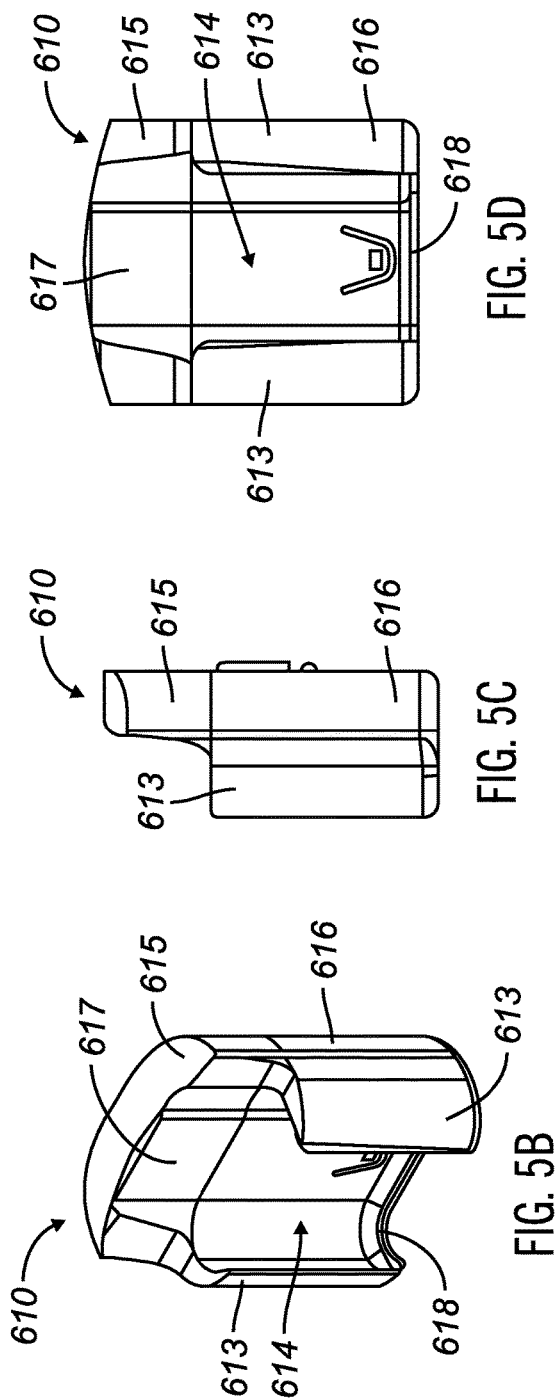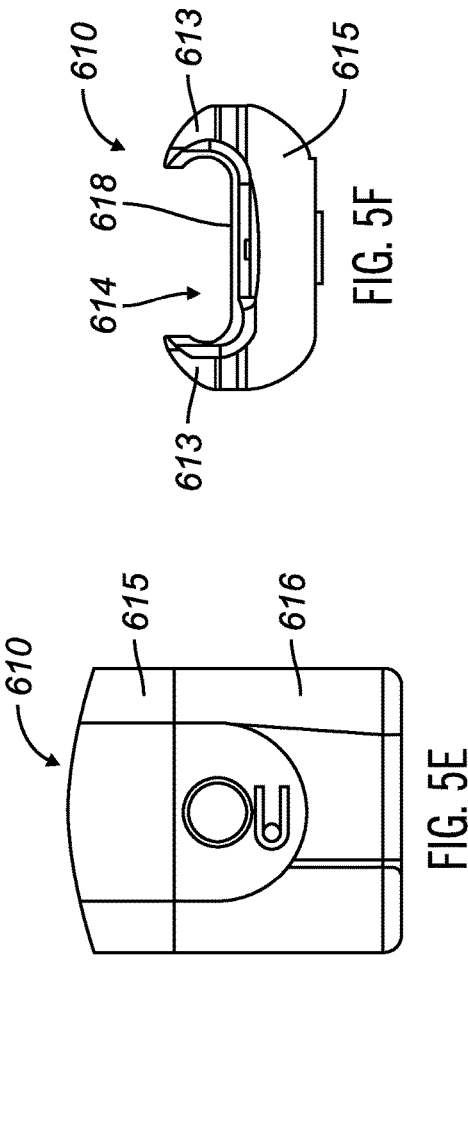

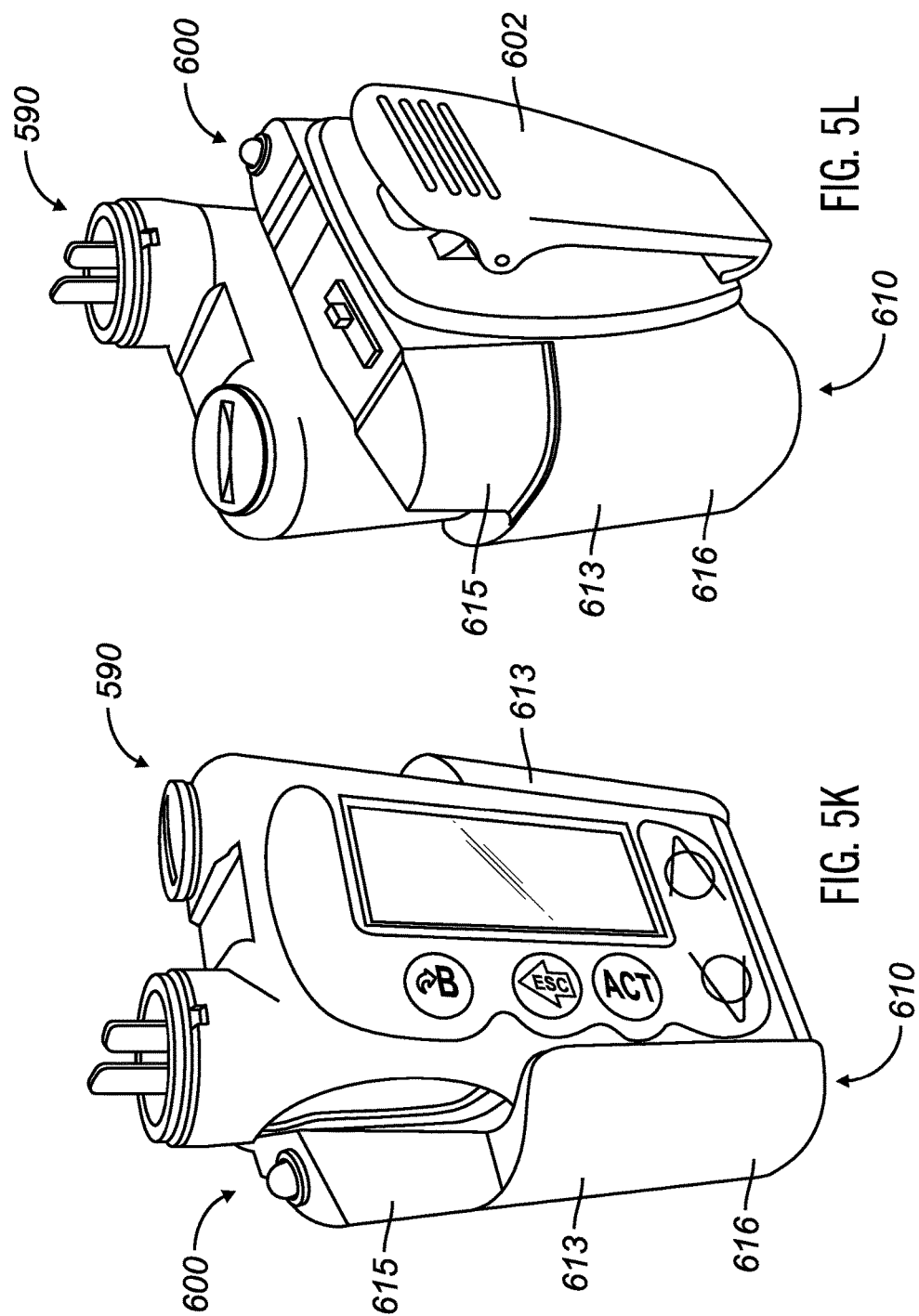

US 9,841,014 B2

INSULIN PUMP DATA ACQUISITION DEVICE AND SYSTEM

CROSS REFERENCE TO RELATED APPLICATIONS

This application is a continuation in part of U.S. patent application Ser. No. 14/518,878, filed on Oct. 20, 2014, and incorporated herein in its entirety by reference.

TECHNICAL FIELD

The technical field of this disclosure is qualitative testing devices, particularly, insulin pump data acquisition devices and system.

BACKGROUND OF THE INVENTION

Advances in electronics and telemetry have resulted in the miniaturization of medical devices such that medical devices which previously required large stationary equipment can now be worn about the person, who can be monitored or receive treatment while pursuing normal daily tasks.

One area of such advances has been in the treatment of diabetes. An estimated twenty-six million people in the United States, or about 8% of the population, have diabetes. This percentage is expected to increase in the near-term as the population ages. Wearable glucose monitors and insulin pumps have been developed which allow persons under treatment for diabetes to be monitored and receive insulin while carrying on their day-to-day tasks.

Although many insulin pumps are in use in the field, detailed information on the conditions under which the insulin pumps operate is limited. At best, some post-failure data is manufactured by analysis of defective insulin pumps after they are returned. Unfortunately, such data is highly speculative and does not provide the detailed information on the conditions to which the insulin pumps during day-to-day activities, such as walking or running. Lack of detailed day-to-day information limits improvement of the insulin pumps to meet real-world conditions: additional expense results from over-design where actual conditions are less severe than assumed conditions and additional failures result from under-design where actual conditions are more severe than assumed design conditions.

It would be desirable to have an insulin pump data acquisition device and system that would overcome the above disadvantages.

SUMMARY OF THE INVENTION

One aspect of the invention provides an insulin pump data acquisition device for use with an insulin pump including: a holster having a wall defining an interior volume and an exterior volume, the exterior volume being sized to removably secure the insulin pump; an environmental sensor operable to generate environmental data in response to environmental conditions; memory operably connected to the environmental sensor, the memory being operable to store the environmental data; a controller operably connected to the environmental sensor and the memory, the controller being operable to control reading of the environmental data from the environmental sensor and writing of the environmental data to the memory; and a battery operably connected to power the environmental sensor, the memory, and the controller. The environmental sensor, the memory, the controller, and the battery are disposed within the interior volume.

Another aspect of the invention provides an insulin pump data acquisition system including: an insulin pump; a holster having walls defining an interior volume and an exterior volume, the exterior volume being sized to removably secure the insulin pump; an environmental sensor operable to generate environmental data in response to environmental conditions; memory operably connected to the environmental sensor, the memory being operable to store the environmental data; a controller operably connected to the environmental sensor and the memory, the controller being operable to control reading of the environmental data from the environmental sensor and writing of the environmental data to the memory; and a battery operably connected to power the environmental sensor, the memory, and the controller. The environmental sensor, the memory, the controller, and the battery are disposed within the interior volume.

Yet another aspect of the invention provides an insulin pump data acquisition device including: an insulin pump casing having an interior volume; an environmental sensor operable to generate environmental data in response to environmental conditions; memory operably connected to the environmental sensor, the memory being operable to store the environmental data; a controller operably connected to the environmental sensor and the memory, the controller being operable to control reading of the environmental data from the environmental sensor and writing of the environmental data to the memory; and a battery operably connected to power the environmental sensor, the memory, and the controller. The environmental sensor, the memory, the controller, and the battery are disposed within the interior volume, and the environmental sensor is selected from the group consisting of a single axis accelerometer, a multi-axis accelerometer, a temperature sensor, a humidity sensor, a pressure sensor, an ultraviolet sensor, and an electromagnetic sensor.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

BRIEF DESCRIPTION OF THE DRAWINGS

FIGS. 5B-5G are schematic diagrams of the holster of an insulin pump data acquisition device as illustrated in FIG. 5A.

FIGS. 5H-5L are photographs of the embodiment of an insulin pump data acquisition device as illustrated in FIG. 5A.

DETAILED DESCRIPTION

Figure 1:
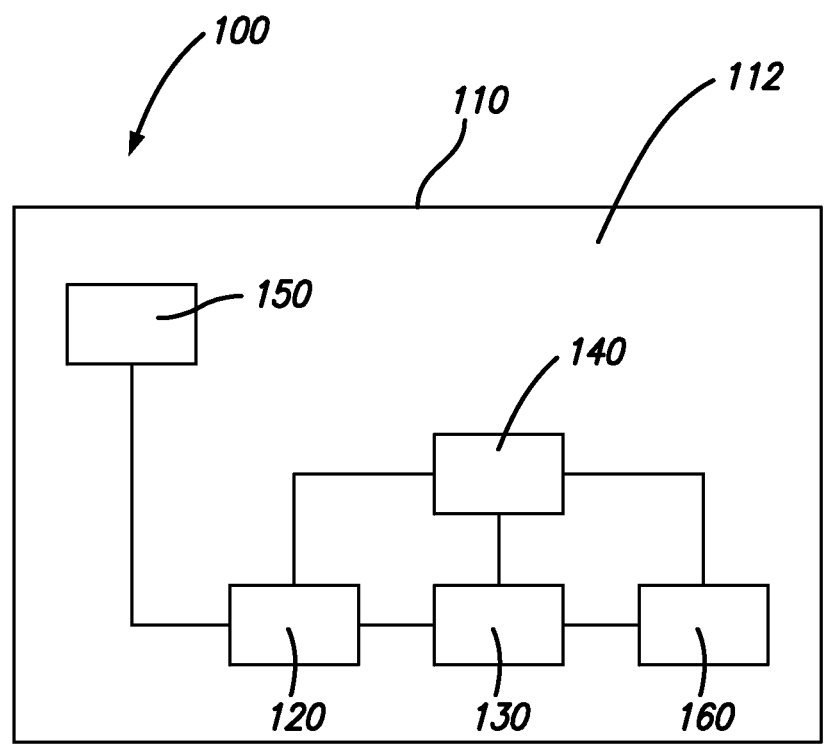
FIG. 1 is a schematic diagram of an insulin pump data acquisition device made in accordance with the invention.

FIG. 1 is a schematic diagram of an insulin pump data acquisition device made in accordance with the invention. The insulin pump data acquisition device 100 can acquire and store environmental data for an insulin device under real-world conditions.

The insulin pump data acquisition device 100 includes an insulin pump casing 110 having an interior volume 112; an environmental sensor 120 operable to generate environmental data in response to environmental conditions; memory 130 operably connected to the environmental sensor 120, the memory 130 being operable to store the environmental data; a controller 140 operably connected to the environmental sensor 120 and the memory 130, the controller 140 being operable to control reading of the environmental data from the environmental sensor 120 and writing of the environmental data to the memory 130; and a battery 150 operably connected to power the environmental sensor 120, the memory 130, and the controller 140. The environmental sensor 120, the memory 130, the controller 140, and the battery 150 are disposed within the interior volume 112 of the insulin pump casing 110. The insulin pump acquisition device 100 can also include an optional input/output feature 160 to transfer programming instructions into and environmental data out of the insulin pump data acquisition device 100.

The insulin pump casing 110 as defined and used herein can be any insulin pump casing used for a prototype or production version of an insulin pump. The interior volume 112 can be the volume as designed to receive other insulin pump components for can be modified to allow additional space for the insulin pump data acquisition device components, i.e., environmental sensor 120, the memory 130, the controller 140, and the battery 150 which are disposed within the interior volume 112.

The environmental sensor 120 can be any sensor operable to generate environmental data in response to environmental conditions. The environmental sensor 120 can be sensitive to conditions around or forces acting on the insulin pump data acquisition device 100. Exemplary environmental sensors include single axis accelerometers, multi-axis accelerometers, temperature sensors, humidity sensors, pressure sensors, and the like. The insulin pump data acquisition device 100 can include one or more environmental sensors as desired for a particular application.

The memory 130 is operably connected to the environmental sensor 120 to store the environmental data received from the environmental sensor 120. The memory 130 can store the environmental data over a period of time until the user desires to read and make use of the stored environmental data. In one example, the memory 130 is nonvolatile memory, such as flash memory or the like, in a compact format such as microSD or the like. The storage capacity of the memory 130 can be selected to store the desired number of data points of environmental data. The environmental data can be stored in any format desired, such as comma separated value format or the like. The stored data can also include a real time clock for each data point provided by the controller 140 and used to determine the time when each data point of environmental data was taken.

The controller 140 is operably connected to the environmental sensor 120 and the memory 130, to control reading of the environmental data from the environmental sensor 120 and writing of the environmental data to the memory 130. In one embodiment, the controller 140 is a microcontroller, i.e., a small computer on a single integrated circuit containing a processor core, memory, and programmable input/output peripherals. In one embodiment, the controller 140 is reprogrammable to set the frequency of the reading of the environmental data to the frequency desired for a particular application. When the insulin pump data acquisition device 100 includes more than one environmental sensor, the insulin pump data acquisition device 100 can also include one or more controllers dedicated to the operation of each environmental sensor.

The battery 150 is operably connected to power the environmental sensor 120, the memory 130, and the controller 140. The battery 150 can be any battery with sufficient voltage and capacity desired for a particular application. Exemplary battery types include nickel-cadmium (NiCd), nickel-zinc (NiZn), nickel metal hydride (NiMH), lithium-ion (Li-ion), lithium polymer, alkaline, and the like. In one embodiment, the battery 150 can be rechargeable.

The insulin pump data acquisition device 100 can also include an optional input/output element 160 to transfer programming instructions into and environmental data out of the insulin pump data acquisition device 100. In one embodiment, the input/output element 160 is a USB plug. In another embodiment, the input/output element is a radio frequency receiver/transmitter.

Figure 2A:
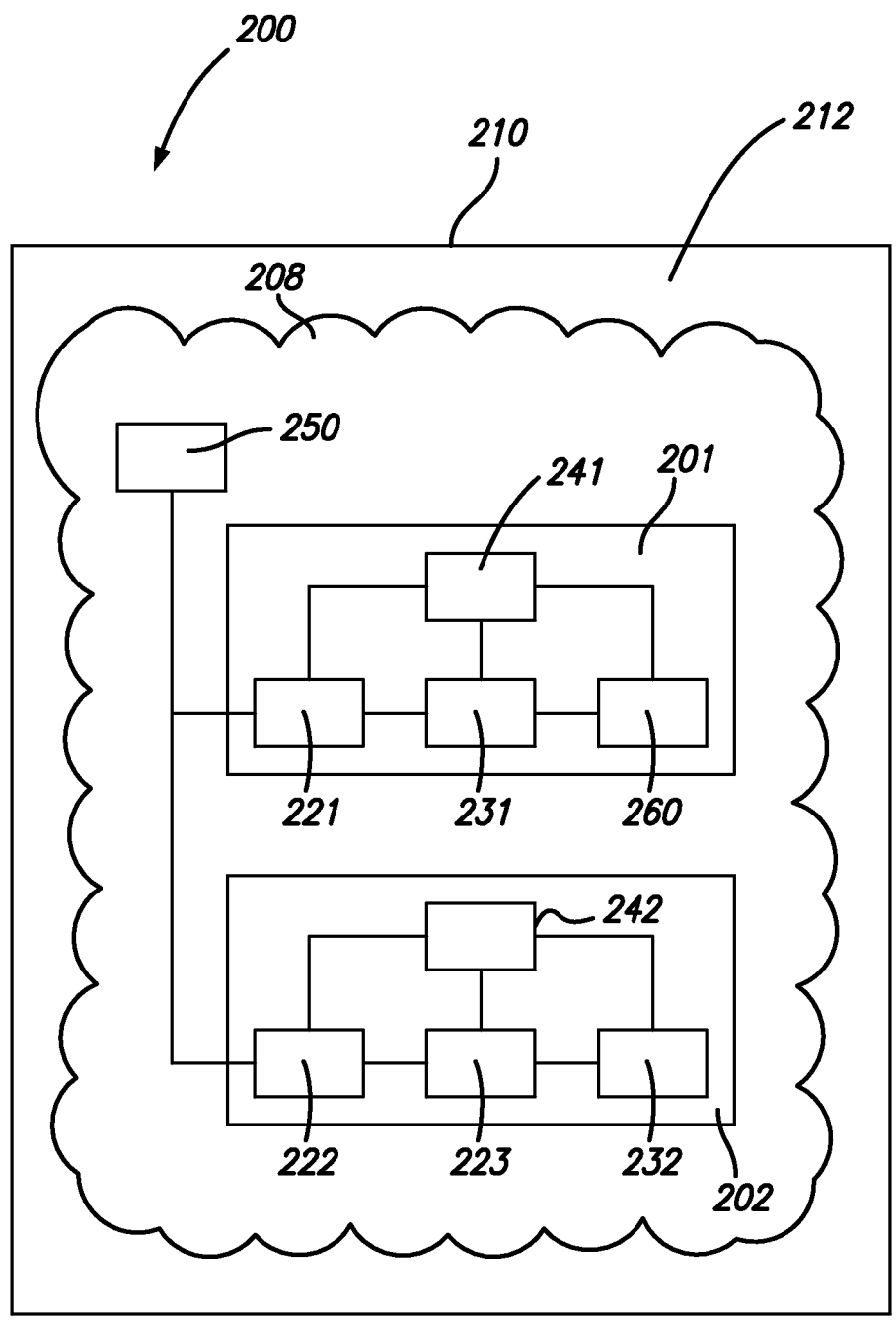
FIG. 2A is a schematic diagram of one embodiment of an insulin pump data acquisition device made in accordance with the invention

FIG. 2A is a schematic diagram of one embodiment of an insulin pump data acquisition device made in accordance with the invention. In this embodiment, the insulin pump data acquisition device includes two controllers and three environmental sensors operable to measure the environmental conditions of multi-axis acceleration, pressure, and temperature.

The insulin pump data acquisition device 200 includes an insulin pump casing 210 having an interior volume 212. The insulin pump data acquisition device components 208 include battery 250, acceleration board 201, and barometer/thermometer board 202 disposed within the interior volume 212. Battery 250 is operably connected to power the components on both the acceleration board 201 and the barometer/thermometer board 202. The acceleration board 201 includes an acceleration sensor 221, removable microSD memory 231, controller 241, and USB plug 260 as an input/output feature (the USB plug 260 being accessible through the insulin pump casing 210). The barometer/thermometer board 202 includes a pressure sensor 222 and a temperature sensor 223, removable microSD memory 232 as memory and an input/output feature (the removable microSD memory 232 being accessible through a port in the insulin pump casing 210), and controller 242.

Figure 2B:
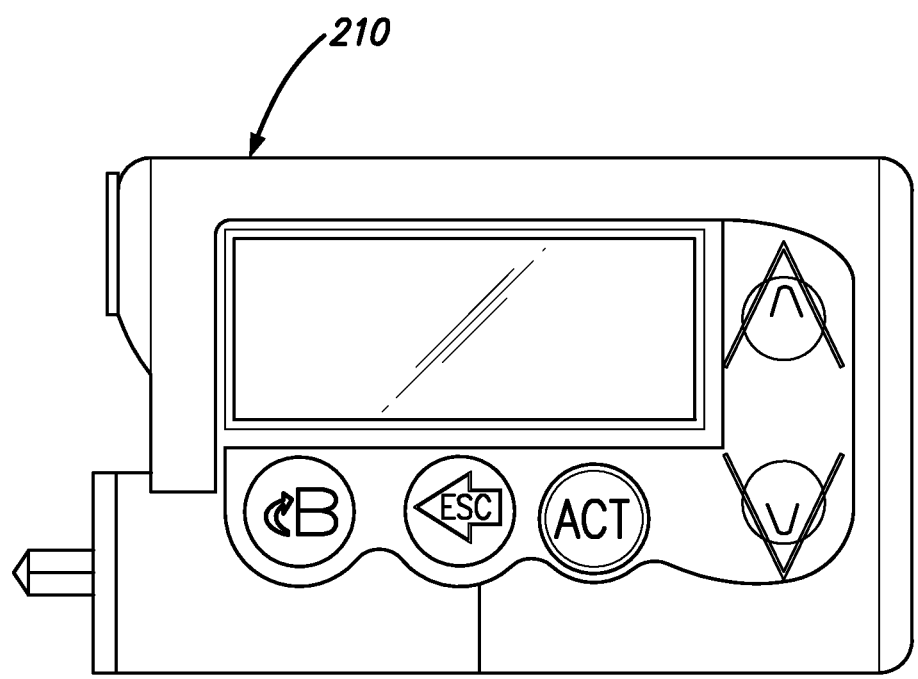
FIGS. 2B-2H are photographs of the embodiment of an insulin pump data acquisition device as illustrated in FIG. 2A.
Figure 2C:
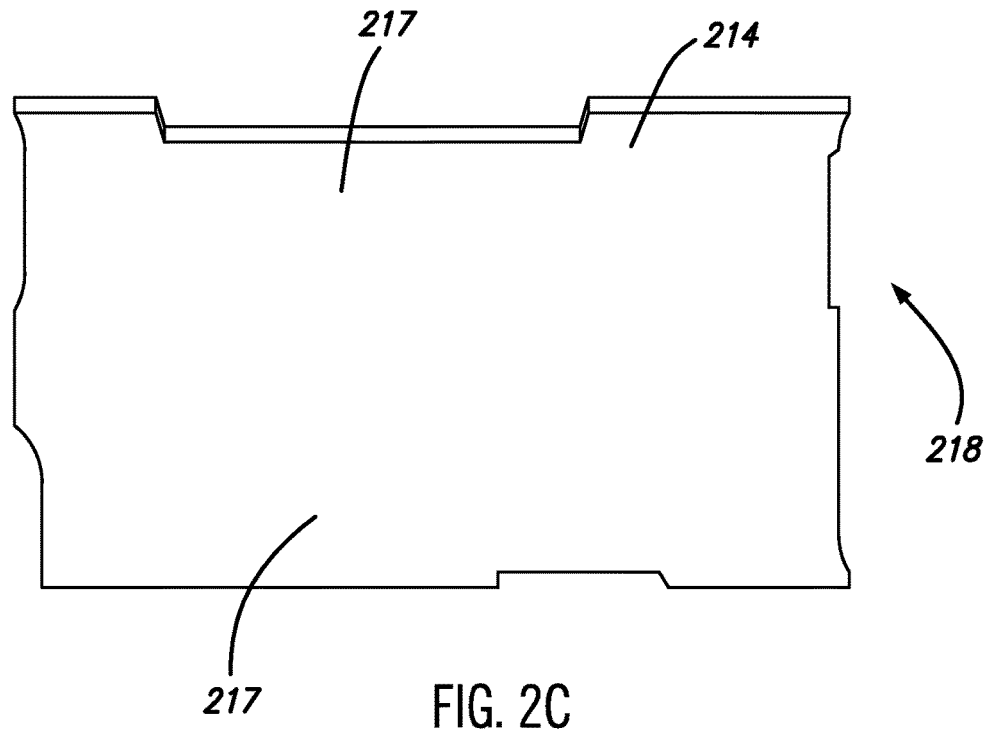
Figure 2D:
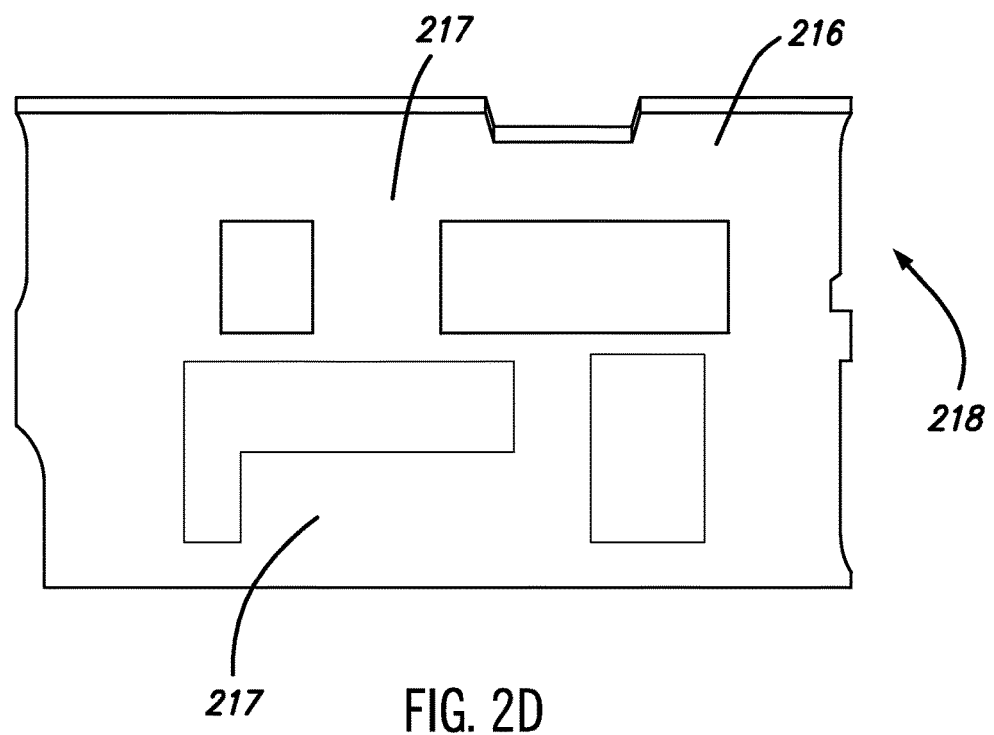
Figure 2E:
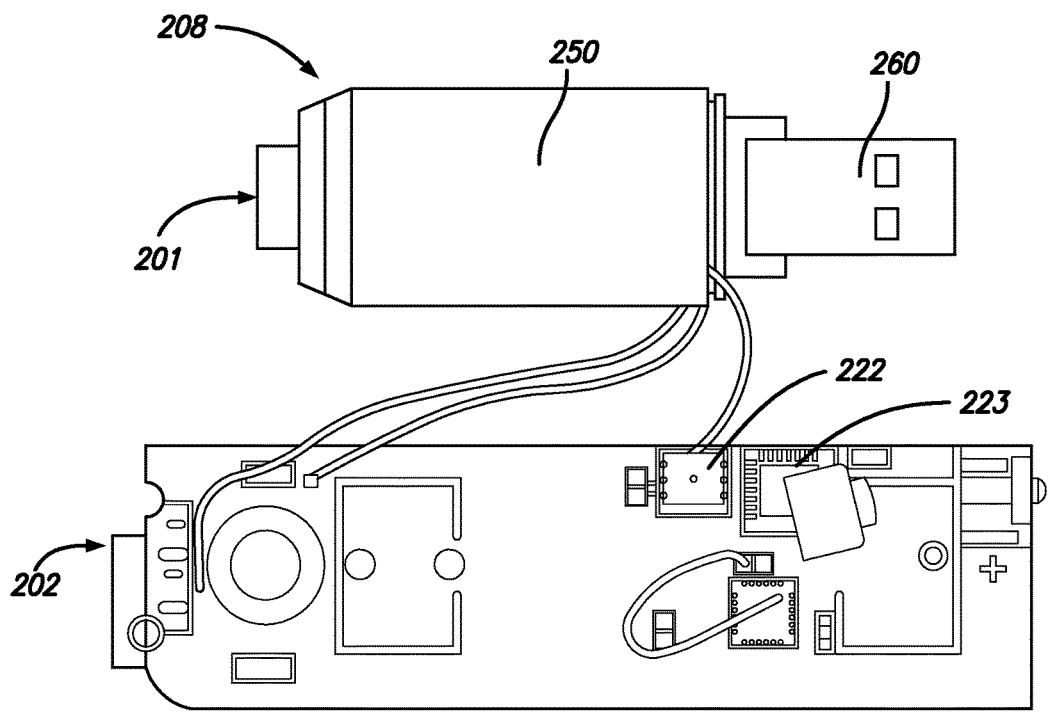
Figure 2F:
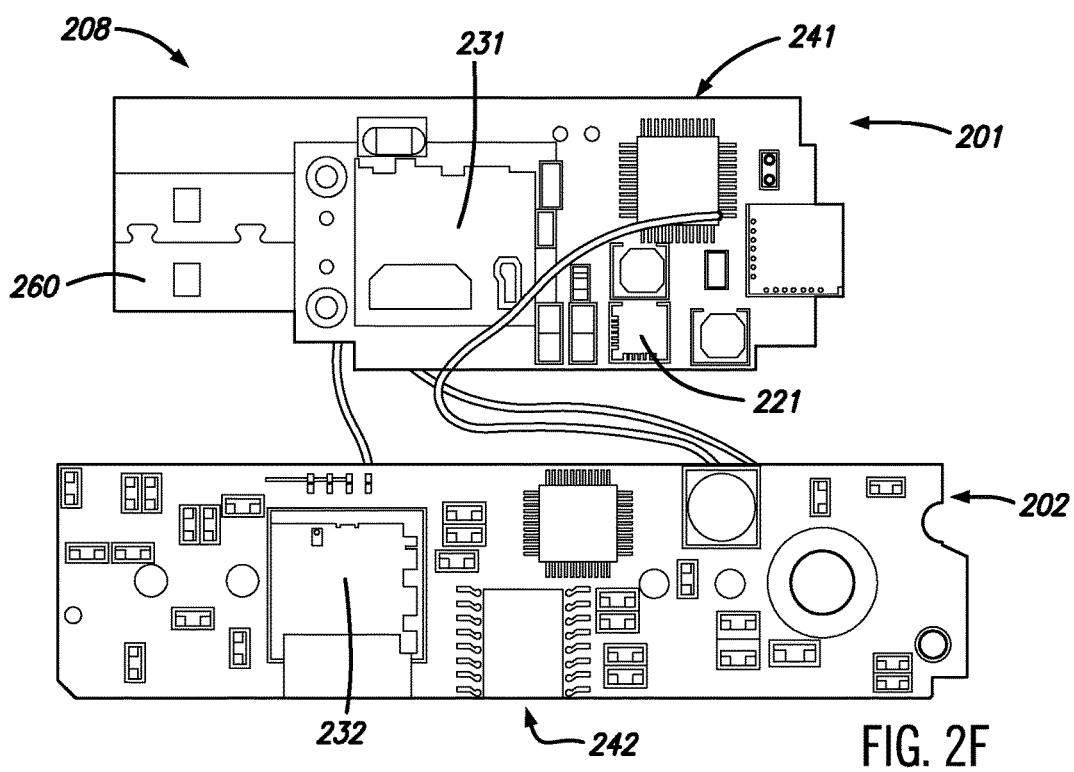
Figure 2G:
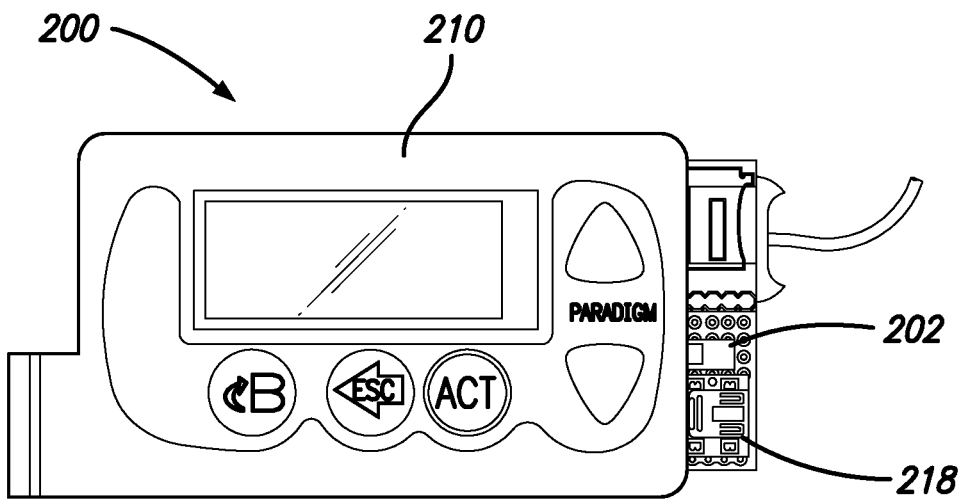
Figure 2H:
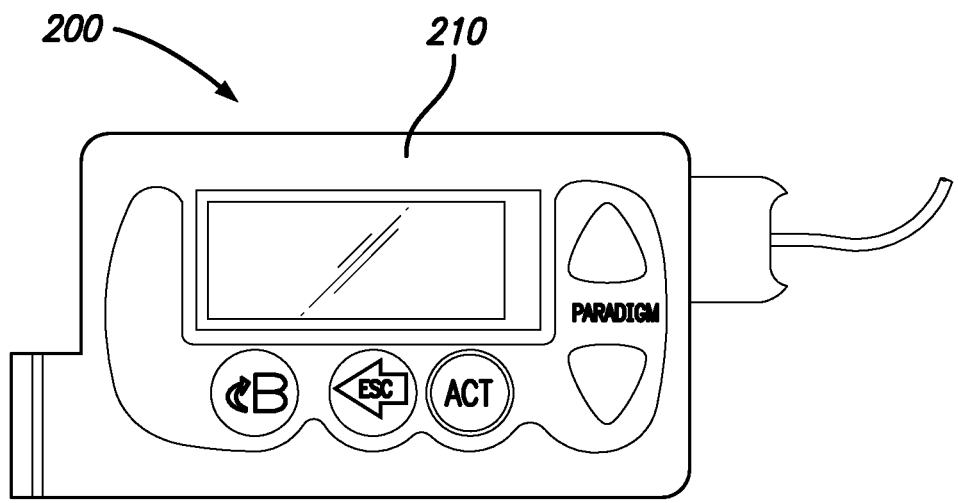

FIGS. 2B-2H, in which like elements share like reference numbers with FIG. 2A, are photographs of one embodiment of an insulin pump data acquisition device made in accordance with the invention. FIGS. 2B-2H are as follows: FIG. 2B is a photograph of an insulin pump casing; FIGS. 2C & 2D are photographs of bottom and top parts, respectively, of a clamshell for an insulin pump data acquisition device; FIGS. 2E & 2F are photographs of a top and bottom view, respectively, of an insulin pump data acquisition device components for an insulin pump data acquisition device; FIGS. 2G & 2H are photographs of a partially assembled and assembled insulin pump data acquisition device, respectively.

Referring to FIG. 2B, insulin pump casing 210 is an insulin pump casing used for a production version of an insulin pump, such as the Medtronic MiniMed Paradigm Revel Insulin Pump. The interior of the production version includes structure to support the insulin pump components, such as the motor, pump, et cetera. In this embodiment of the insulin pump data acquisition device, the support structure is removed so that only the outside wall remains to form the interior volume (not shown). Those skilled in the art will appreciate that the interior of the production or prototype version of the insulin pump casing can be modified as desired for a particular application to accommodate the insulin pump data acquisition device components disposed within the interior volume.

FIGS. 2C & 2D are photographs of bottom and top parts, respectively, of a clamshell for an insulin pump data acquisition device. In this embodiment, the clamshell 218 including the bottom clamshell 214 and the top clamshell 216 fit together to hold the insulin pump data acquisition device components and to fill the space between the insulin pump casing and the insulin pump data acquisition device components within the interior volume. The bottom clamshell 214 and the top clamshell 216 include recesses 217 sized to accept the insulin pump data acquisition device components. The exterior of the clamshell 218 is sized to fit firmly within the insulin pump casing. Those skilled in the art will appreciate that a firm fit can be desirable for certain environmental sensors, such as accelerometers and the like. The clamshell 218 and the insulin pump casing can optionally include ports and/or openings to allow access to the insulin pump data acquisition device components for environmental data measurement, power input, data output (telemetrically, electronically, or microSD card retrieval), programming input, and the like.

FIGS. 2E & 2F are photographs of a top and bottom view, respectively, of insulin pump data acquisition device components for an insulin pump data acquisition device. The insulin pump data acquisition device components 208 include an acceleration board 201 and a barometer/thermometer board 202. Battery 250 mounted on the acceleration board 201 is operably connected to power the components on both the acceleration board 201 and the barometer/thermometer board 202.

The acceleration board 201 includes an acceleration sensor 221 as the environmental sensor, removable microSD memory 231 as the memory, controller 241, the battery 250, and USB plug 260 as the input/output feature. The acceleration sensor 221 in this example is a three axis accelerometer and is operable to generate acceleration data in response to acceleration conditions on the insulin pump data acquisition device. The removable microSD memory 231 is operable to store the acceleration data from the acceleration sensor 221. The controller 241 is operable to control reading of the acceleration data from the acceleration sensor 221 and to control writing of the acceleration data to the removable microSD memory 231. The USB plug 260 is operable to download the acceleration data from the removable microSD memory 231 to external devices. The USB plug 260 is also operable to receive programming instructions from external devices to program operating parameters for the acceleration board 201, such as the frequency of reading the acceleration data. The acceleration data can also be transferred by removal of the microSD card from the removable microSD memory 231 and transfer of the microSD card to an external device.

In this example, the acceleration board 201 is a modified version of a X6-2mini USB Accelerometer manufactured by Gulf Coast Data Concepts, LLC, of Waveland, Miss. The acceleration board 201 has a 0-320 Hz sample rate; 3-axis+/−6 g range and 2% full scale linearity for the acceleration sensor. The battery 250 is a 250 mAh lithium-polymer battery rechargeable through the USB plug 260. Those skilled in the art will appreciate that different components with different values can be used as desired for a particular application.

The barometer/thermometer board 202 includes a pressure sensor 222 and a temperature sensor 223 as the environmental sensors, removable microSD memory 232 as the memory and as the input/output feature, and controller 242. The pressure sensor 222 in this example is operable to generate pressure data in response to pressure conditions on the insulin pump data acquisition device. The temperature sensor 223 in this example is operable to generate temperature data in response to temperature conditions on the insulin pump data acquisition device. The removable microSD memory 232 is operable to store the pressure data from the pressure sensor 222 and the temperature data from the temperature sensor 223. The controller 241 is operable to control reading of the pressure data and temperature data, and to control writing of the pressure data and temperature data to the removable microSD memory 232. The pressure data and temperature data can be transferred to an external device by removal of the microSD card from the removable microSD memory 232 and transfer of the microSD card to an external device. The barometer/thermometer board 202 is powered by the battery 250 physically attached to the acceleration board 201.

In this example, the barometer/thermometer board 202 is a modified version of a B1100-1 Barometric Pressure USB Data Logger manufactured by Gulf Coast Data Concepts, LLC, of Waveland, Miss. The barometer/thermometer board 202 has a 0-10 Hz sample rate; for the pressure sensor, 30-110 kPa range with +/−100 kPa typical accuracy throughout the range; and for the temperature sensor, 0-65 degrees C. range with +/−1 degree C. typical accuracy. Those skilled in the art will appreciate that different components with different values can be used as desired for a particular application.

FIGS. 2G & 2H are photographs of a partially assembled and assembled insulin pump data acquisition device, respectively. Referring to FIG. 2G, the barometer/thermometer board 202 and acceleration board (not shown) are located within recesses in the clamshell 218, which is partially inserted into the insulin pump casing 210. Referring to FIG. 2H, the clamshell is fully inserted within the insulin pump casing 210 to form the insulin pump data acquisition device 200. Those skilled in the art will appreciate that the components can be secured within the insulin pump casing 210 with adhesive, mechanical fittings, or the like, as desired for a particular application. In use, the insulin pump data acquisition device can be worn by the patient in the same manner as an actual insulin pump and environmental data recovered from the insulin pump data acquisition device to analyze environmental conditions to which the insulin pump data acquisition device standing in for the insulin pump has been exposed.

Figure 3A:
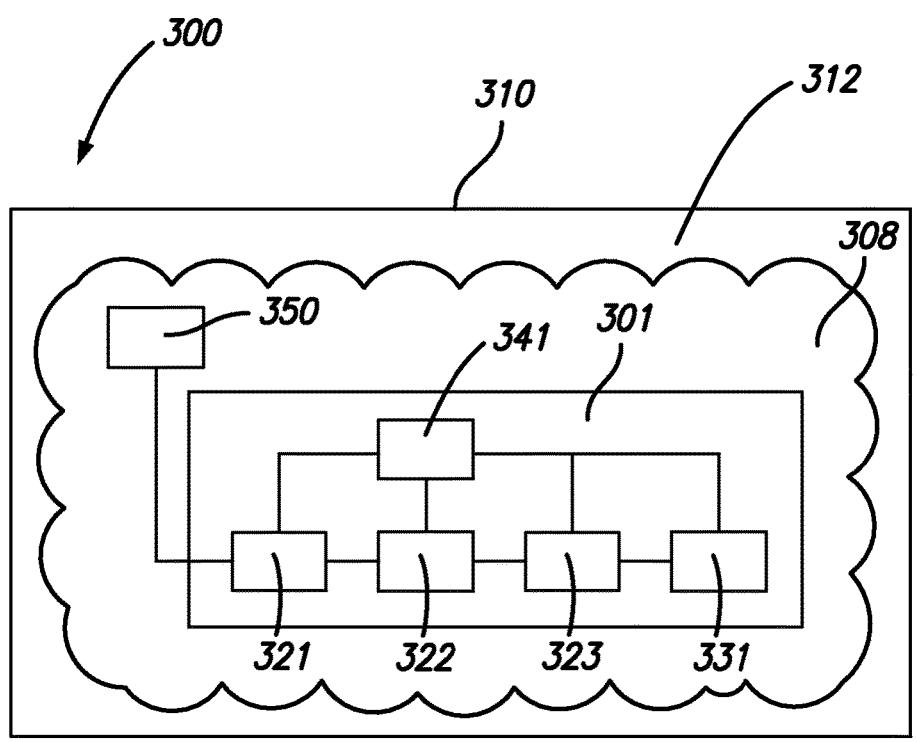
FIG. 3A is a schematic diagram of one embodiment of an insulin pump data acquisition device made in accordance with the invention.

FIG. 3A is a schematic diagram of one embodiment of an insulin pump data acquisition device made in accordance with the invention. In this embodiment, the insulin pump data acquisition device includes one controller and three environmental sensors operable to measure the environmental conditions of multi-axis acceleration, pressure, and temperature/humidity.

The insulin pump data acquisition device 300 includes an insulin pump casing 310 having an interior volume 312. The insulin pump data acquisition device components 308 include battery 350 and circuit board 301 disposed within the interior volume 312. The circuit board 301 includes an acceleration sensor 321, a pressure sensor 322, and a temperature/humidity sensor 323, removable microSD memory 331 as memory and an input/output feature (the removable microSD memory 331 being accessible through a port in the insulin pump casing 310), and controller 341.

Figure 3B:
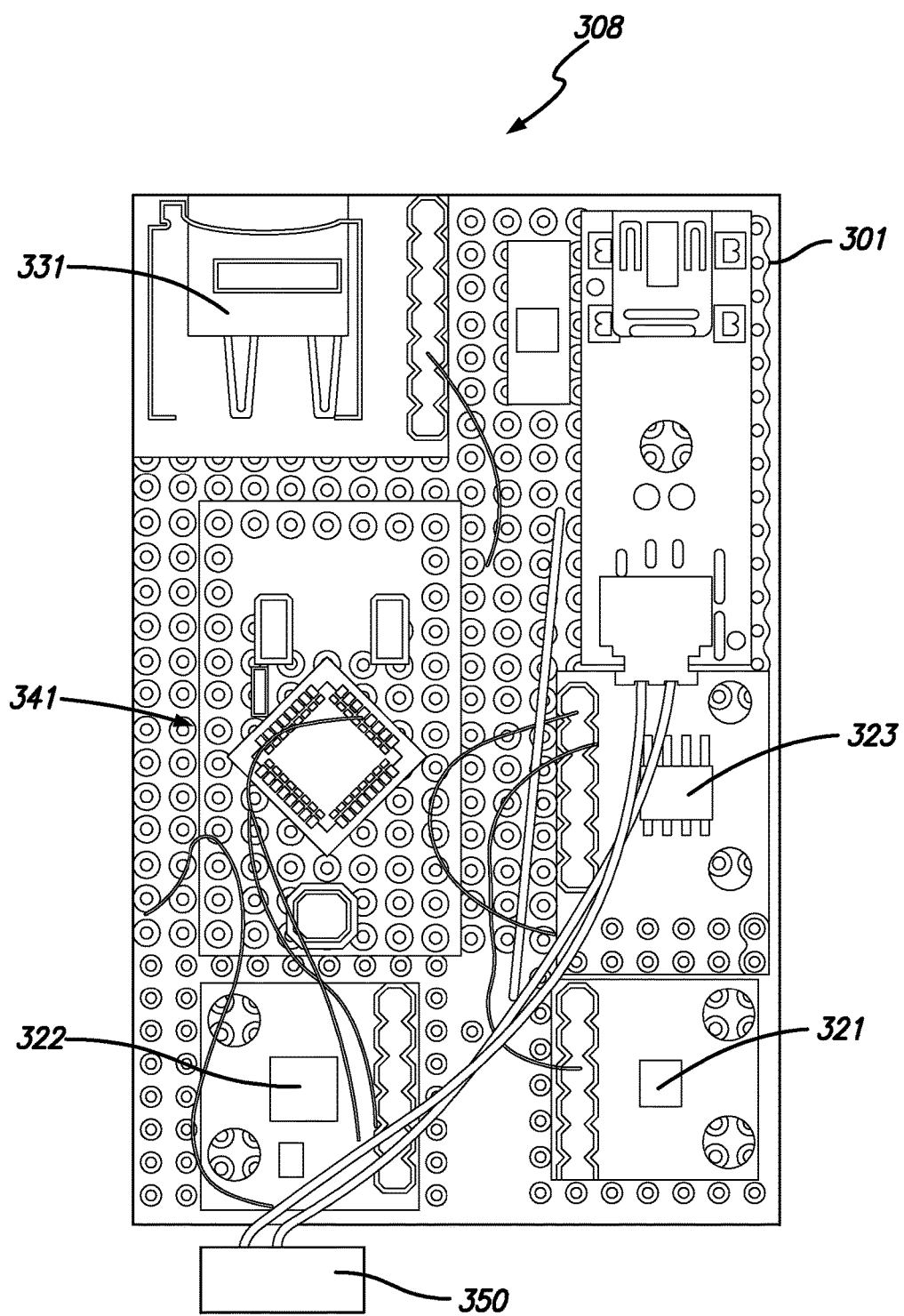
FIGS. 3B-3D are photographs of the embodiment of an insulin pump data acquisition device as illustrated in FIG. 3A.
Figure 3C:
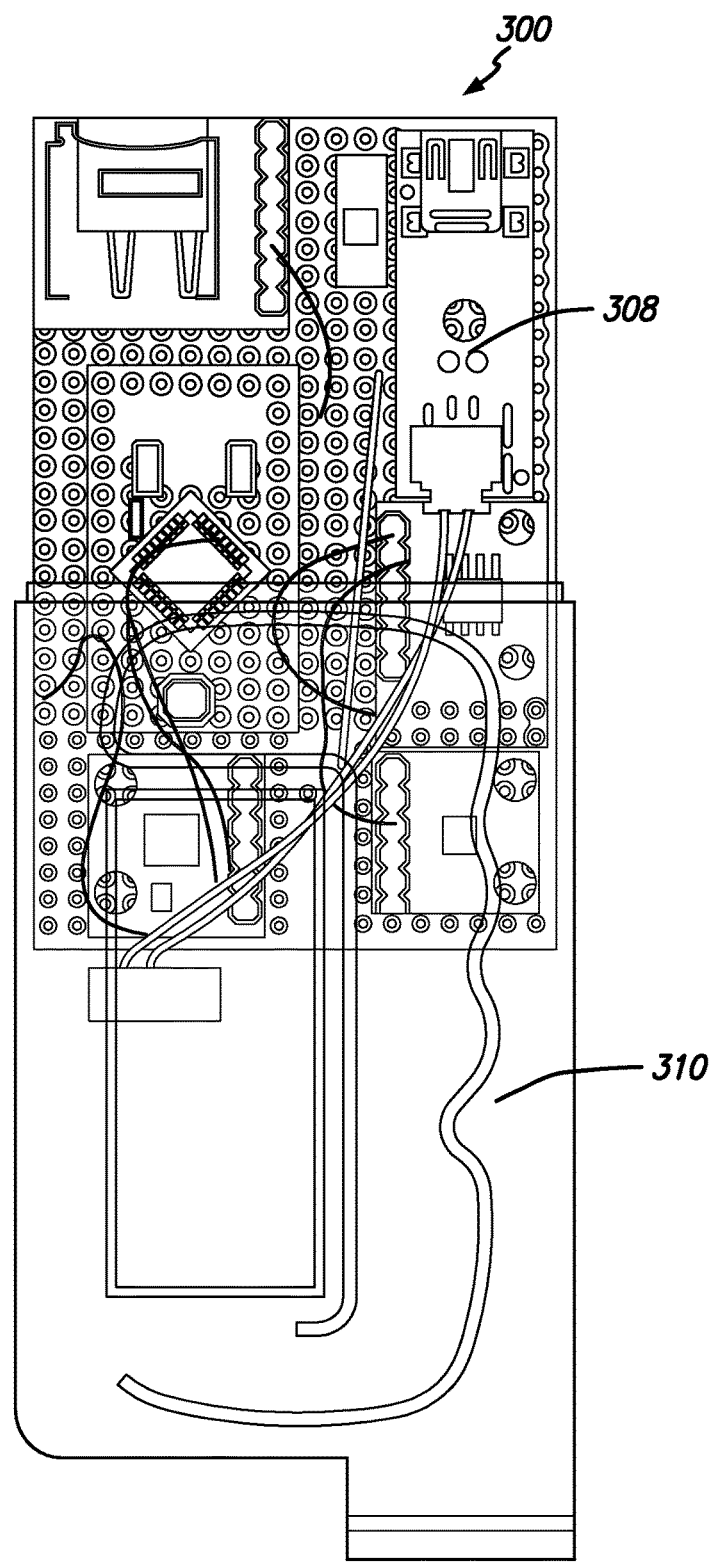
Figure 3D:
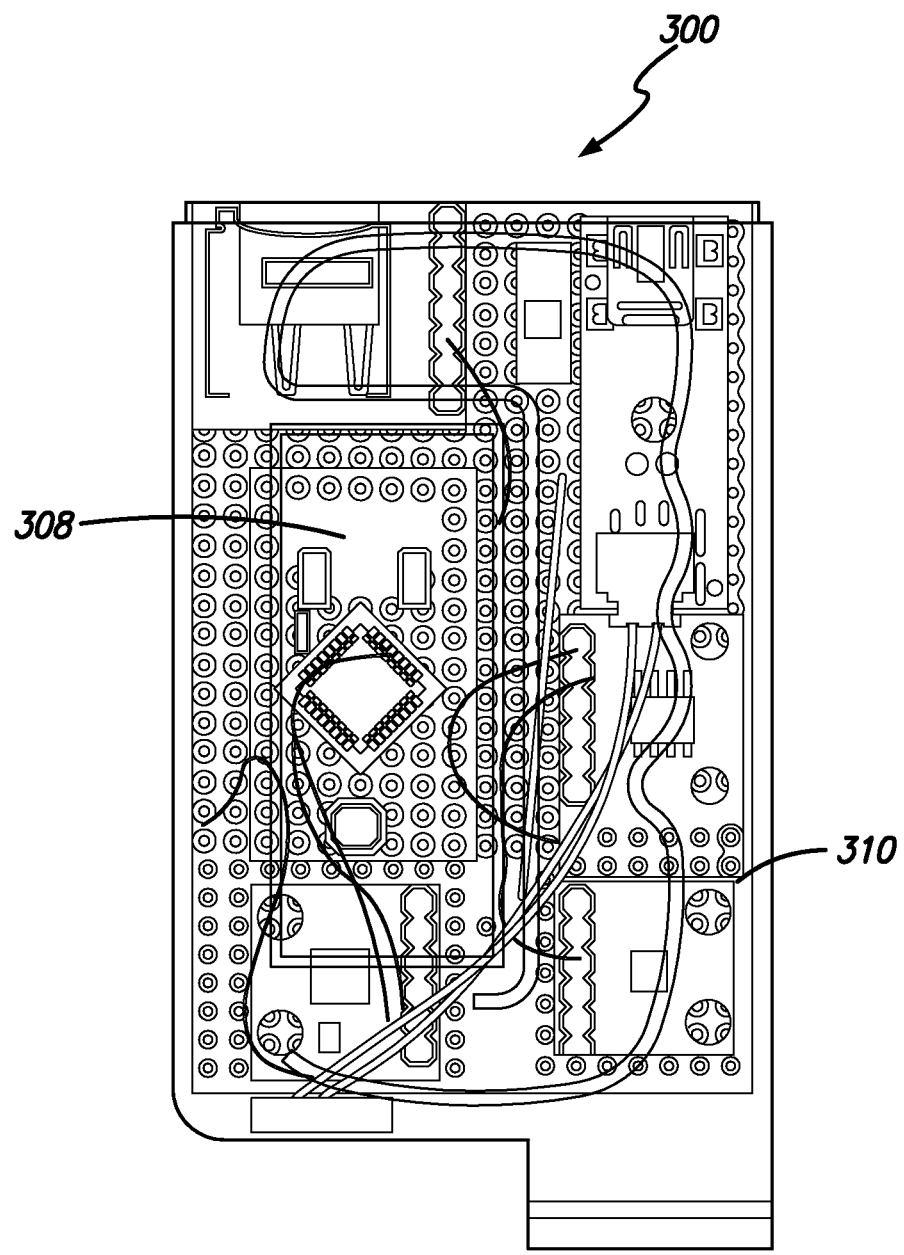

FIGS. 3B-3D are photographs of the embodiment of an insulin pump data acquisition device as illustrated in FIG. 3A. FIG. 3B is a photograph of insulin pump data acquisition device components for an insulin pump data acquisition device. FIGS. 3C & 3D are photographs of a partially assembled and assembled insulin pump data acquisition device, respectively.

Referring to FIG. 3B, the circuit board 301 includes an acceleration sensor 321, a pressure sensor 322, and a temperature/humidity sensor 323, removable microSD memory 331, and controller 341. The acceleration sensor 321 in this example is a three axis accelerometer and is operable to generate acceleration data in response to acceleration conditions on the insulin pump data acquisition device. The pressure sensor 322 in this example is operable to generate pressure data in response to pressure conditions on the insulin pump data acquisition device. The temperature/humidity sensor 323 in this example is operable to generate temperature data and humidity data in response to data and humidity conditions, respectively, on the insulin pump data acquisition device. The removable microSD memory 331 is operable to store the environmental data, i.e., the acceleration data, pressure data, temperature data, and humidity data. The controller 341 is operable to control reading of the environmental data from the acceleration sensor 321, pressure sensor 322, and temperature/humidity sensor 323 and to control writing of the environmental data to the removable microSD memory 331. The removable microSD memory 331 is operable to store the environmental data. The environmental data can be transferred to an external device by removal of the microSD card from the removable microSD memory 331 and transfer of the microSD card to an external device. The circuit board 301 is powered by the battery 350 external to the circuit board 301. In one embodiment, the battery 350 can be rechargeable.

FIGS. 3C & 3D are photographs of a partially assembled and assembled insulin pump data acquisition device, respectively. Referring to FIG. 3C, the circuit board 301 is partially inserted into the insulin pump casing 310. Referring to FIG. 3D, the circuit board 301 is fully inserted within the insulin pump casing 310 to form the insulin pump data acquisition device 300.

Those skilled in the art will appreciate that the environmental sensors can be selected as desired for a particular application. In this example, the acceleration sensor 321 is a MMA8452Q Low g, 12-bit Digital Accelerometer manufactured by Freescale Semiconductor, Inc., of Austin, Tex. The acceleration sensor 321 is a smart low-power, three-axis, capacitive MEMS accelerometer with 12 bits of resolution with user-selectable full scale ranges of ±2 g/±4 g/±8 g. In this example, the pressure sensor 322 is a BMP085 digital pressure sensor manufactured by Bosch Sensortec GMBH of Reutlingen, Germany. The pressure sensor 322 is a high-precision, low-power digital barometer and has a pressure sensing range of 300-1100 hPa with an accuracy of +/−4 hPa. In this example, the temperature/humidity sensor 323 is a Digital Humidity/Temperature Sensor manufactured by Honeywell Sensing and Control of Morristown, N.J. the temperature/humidity sensor 323 is a digital output-type relative humidity (RH) and temperature sensor combined, with a temperature range from −25 to 85 degrees C. and an accuracy of +/−1 degrees C. and a humidity range from 10% to 90% relative humidity and an accuracy of +/−4% relative humidity.

In this example, the controller 341 is a Arduino Pro Mini 328 single-board microcontroller, manufactured by SparkFun Electronics of Niwot, Colo. The controller 341 uses a ATmega168 microcontroller. The programming for the controller 341 is written in C or C++ and developed on the Arduino integrated development environment (IDE), which is a cross-platform application written in Java. In one embodiment, the programming optimizes battery life. In another embodiment, the programming optimizes environmental sensor sampling rate. In yet another embodiment, the programming balances battery life with environmental sensor sampling rate. In one embodiment when the insulin pump data acquisition device includes a number of environmental sensors, the programming can collect environmental data from preselected environmental sensors of interest for a particular application, rather than collect environmental data from all the environmental sensors. In another embodiment, the programming can collect environmental data from all of the environmental sensors.

Referring to FIG. 3C, the insulin pump data acquisition device components 308 including the battery and circuit board are fully inserted within the insulin pump casing 310 to form the insulin pump data acquisition device 300. The insulin pump casing 310 can optionally include ports and/or openings to allow access to the insulin pump data acquisition device components for environmental data measurement, power input, data output (electronically or microSD card retrieval), programming input, and the like. Those skilled in the art will appreciate that the insulin pump data acquisition device components 308 can be secured within the insulin pump casing 310 with adhesive, mechanical fittings, or the like, as desired for a particular application. In use, the insulin pump data acquisition device can be worn by the patient in the same manner as an actual insulin pump and environmental data recovered from the insulin pump data acquisition device to analyze environmental conditions to which the insulin pump data acquisition device standing in for the insulin pump has been exposed.

Figure 4A:
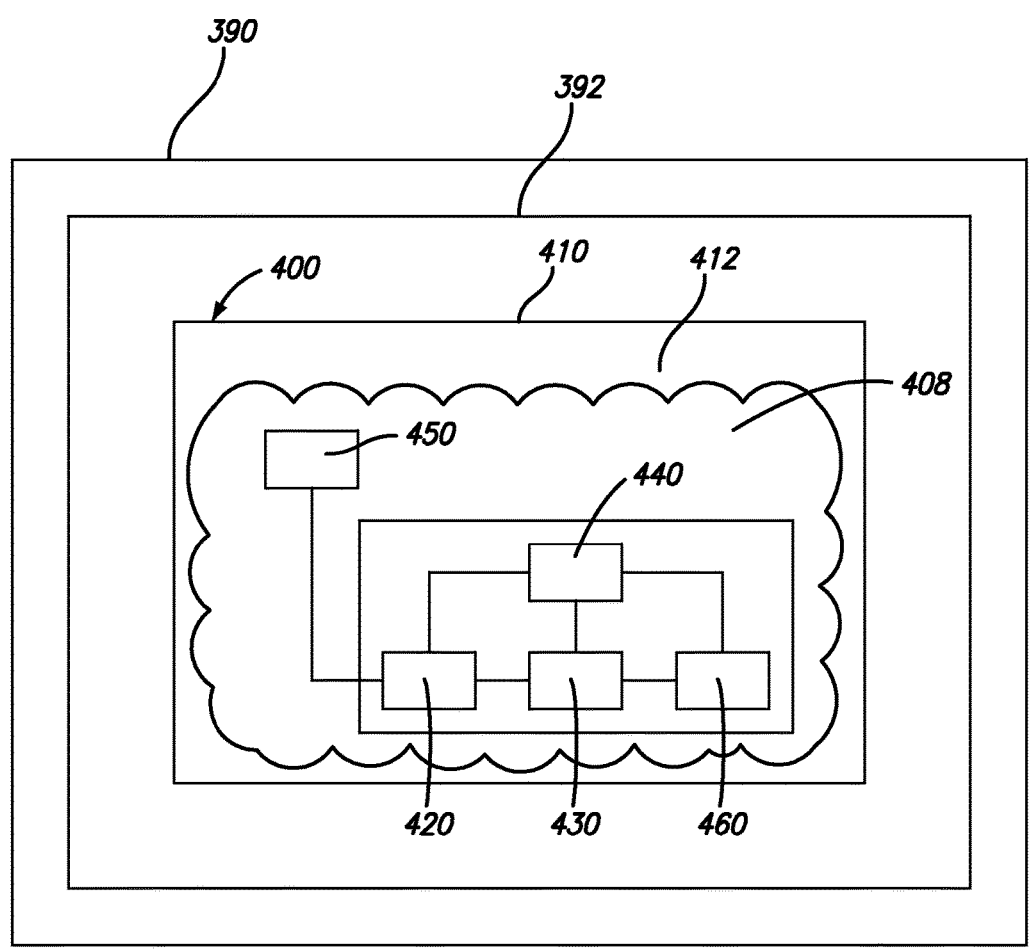
FIGS. 4A & 4B are a schematic diagram and an exploded diagram, respectively, of a data acquisition device made in accordance with the invention.
Figure 4B:
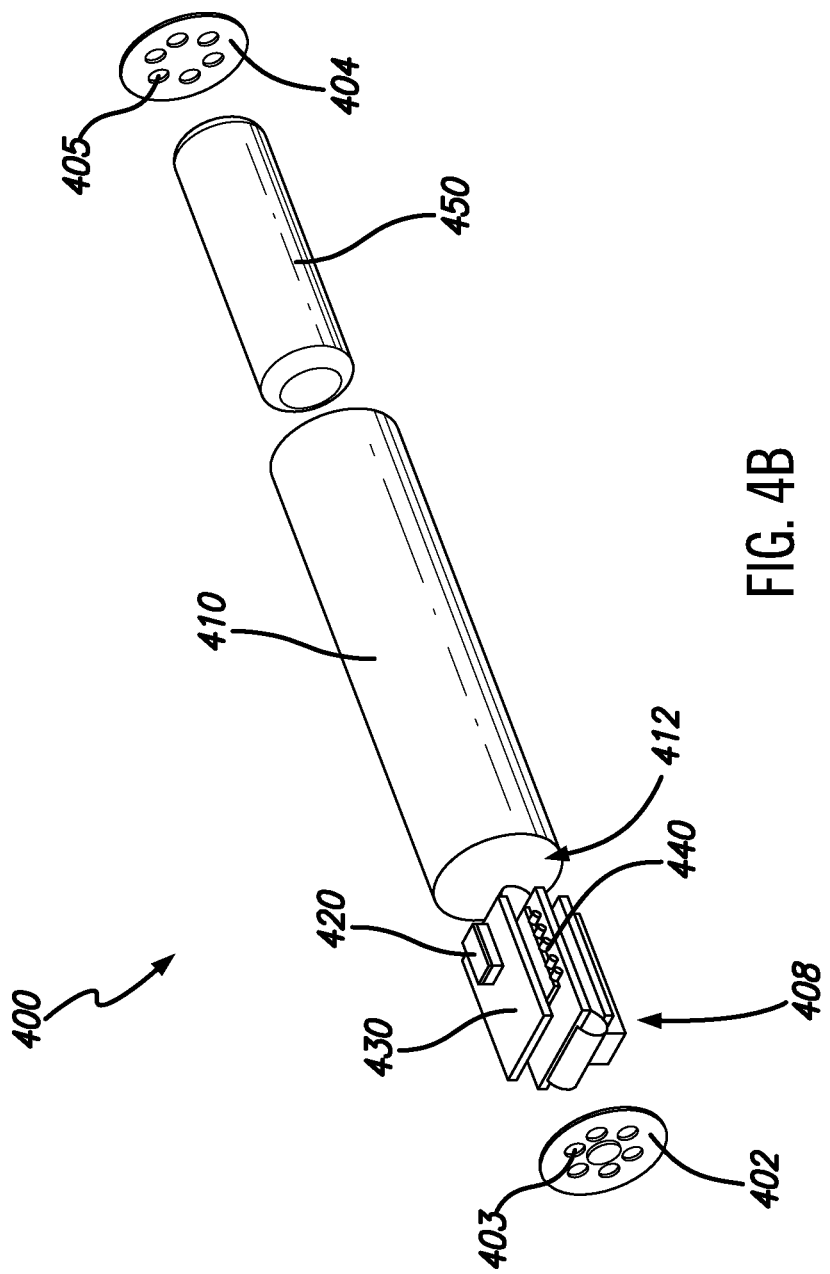

FIGS. 4A & 4B, in which like elements share like reference numbers, are a schematic diagram and an exploded diagram, respectively, of a data acquisition device made in accordance with the invention. The data acquisition device 400 can acquire and store environmental data for an apparatus having a battery compartment under real-world conditions.

The data acquisition device 400 is for use with any apparatus 390 having a battery compartment 392, such as an insulin pump or the like. The data acquisition device 400 includes a battery casing 410 sized to fit within the battery compartment 392, the battery casing 410 having an internal volume 412; an environmental sensor 420 operable to generate environmental data in response to environmental conditions; memory 430 operably connected to the environmental sensor 420, the memory 430 being operable to store the environmental data; a controller 440 operably connected to the environmental sensor 420 and the memory 430, the controller 440 being operable to control reading of the environmental data from the environmental sensor 420 and writing of the environmental data to the memory 430; and a battery 450 operably connected to power the environmental sensor 420, the memory 430, and the controller 440. The environmental sensor 420, the memory 430, the controller 440, and the battery 450 are disposed within the interior volume 412 of the battery casing 410. The insulin pump data acquisition device 400 can also include an optional input/output feature 460 to transfer programming instructions into and environmental data out of the data acquisition device 400.

The battery casing 410 as defined and used herein can be any casing sized to fit within the battery compartment of any battery powered apparatus. The interior volume 412 can include adapters to receive the data acquisition device components 408, i.e., the environmental sensor 420, the memory 430, the controller 440, and the battery 450 which are disposed within the interior volume 412. In one embodiment, the data acquisition device components 408 are mounted on a folded circuit board as illustrated in FIG. 4B, defined herein as rigid portions of printed circuit board joined with ribbon cables. In another embodiment, the data acquisition device components 408 are mounted on a flexible circuit board, defined herein as a circuit board having a flexible substrate and traces, so that the flexible circuit board can be folded or rolled as desired for a particular application.

In one embodiment, the battery casing 410 is same size as a AA battery, a AAA battery, or the like, which is used with the apparatus 390 during normal operation. The ends of the battery casing 410 can be closed with a positive end cap 402 and a negative end cap 404. In one embodiment, the positive end cap 402 and the negative end cap 404 can be connected to the battery 450 to power the apparatus 390 in place of the battery used during normal operation, i.e., the data acquisition device 400 powers the apparatus 390 when the data acquisition device 400 is in use. The positive end cap 402 and the negative end cap 404 can optionally include holes 403 and holes 405, respectively, to allow the environmental sensor 420 to sense environmental conditions outside the data acquisition device 400 and/or to vent heat from the internal components.

The environmental sensor 420 can be any sensor operable to generate environmental data in response to environmental conditions. The environmental sensor 420 can be sensitive to conditions around or forces acting on the data acquisition device 400. Exemplary environmental sensors include single axis accelerometers, multi-axis accelerometers, temperature sensors, humidity sensors, pressure sensors, and the like. The data acquisition device 400 can include one or more environmental sensors as desired for a particular application.

The memory 430 is operably connected to the environmental sensor 420 to store the environmental data received from the environmental sensor 420. The memory 430 can store the environmental data over a period of time until the user desires to read and make use of the stored environmental data. In one example, the memory 430 is nonvolatile memory, such as flash memory or the like, in a compact format such as microSD or the like. The storage capacity of the memory 430 can be selected to store the desired number of data points of environmental data. The environmental data can be stored in any format desired, such as comma separated value format or the like. The stored data can also include a real time clock for each data point provided by the controller 440 and used to determine the time when each data point of environmental data was taken.

The controller 440 is operably connected to the environmental sensor 420 and the memory 430, to control reading of the environmental data from the environmental sensor 420 and writing of the environmental data to the memory 430. In one embodiment, the controller 440 is a microcontroller, i.e., a small computer on a single integrated circuit containing a processor core, memory, and programmable input/output peripherals. In one embodiment, the controller 440 is reprogrammable to set the frequency of the reading of the environmental data to the frequency desired for a particular application. When the insulin pump data acquisition device 400 includes more than one environmental sensor, the insulin pump data acquisition device 400 can also include one or more controllers dedicated to the operation of each environmental sensor.

The battery 450 is operably connected to power the environmental sensor 420, the memory 430, and the controller 440. The battery 450 can be any battery with sufficient voltage and capacity desired for a particular application. Exemplary battery types include nickel-cadmium (NiCd), nickel-zinc (NiZn), nickel metal hydride (NiMH), lithium-ion (Li-ion), lithium polymer, alkaline, and the like. In one embodiment, the battery 450 can be rechargeable. In one embodiment, the battery 450 can operably connected to power the apparatus 390, such as an insulin pump or the like, so that the data acquisition device 400 replaces the normal battery used by the apparatus 390.

The data acquisition device 400 can also include an optional input/output element 460 to transfer programming instructions into and environmental data out of the data acquisition device 400. In one embodiment, the input/output element 460 is a USB plug. In another embodiment, the input/output element 460 is a microSD memory card which can be removed from the data acquisition device 400 and read by an external device. In yet another embodiment, the input/output element is a radio frequency receiver/transmitter.

Figure 4C:
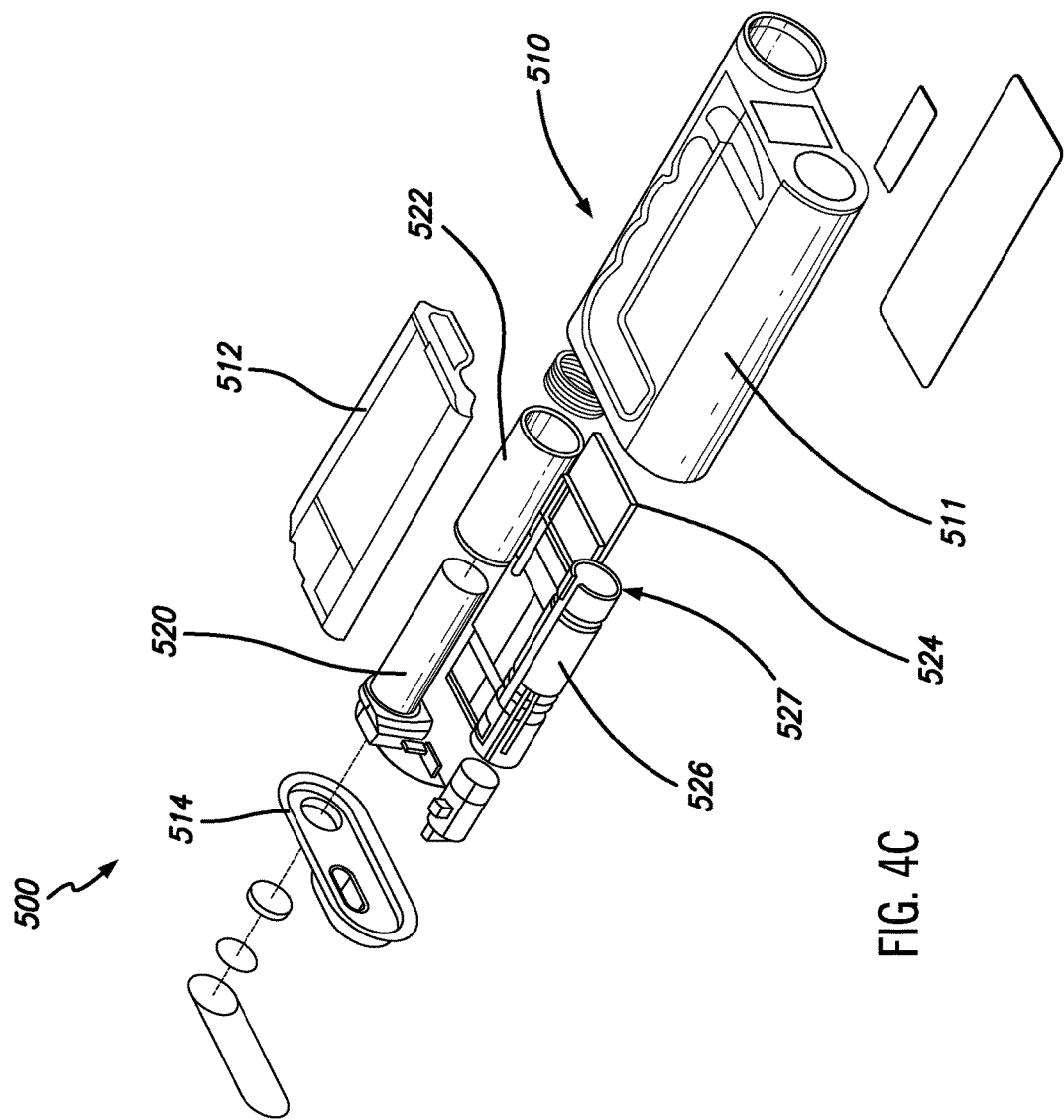
FIG. 4C is an exploded diagram of an insulin pump for use with a data acquisition device made in accordance with the invention.

FIG. 4C is an exploded diagram of an insulin pump for use with a data acquisition device made in accordance with the invention. The insulin pump 500 is an example of an apparatus that can be used with the data acquisition device 400 described in conjunction with FIGS. 4A & 4B above. Those skilled in the art will appreciate that the data acquisition device can be used with any apparatus with a battery compartment.

Referring to FIG. 4C, the insulin pump 500 includes an insulin pump casing 510 with face trim 512 and end cap 514. The insulin pump casing 510 has an insulin pump interior volume 512, which is operable to receive the insulin pump components, including therapeutic agent receiver 522, insulin pump drive 520, insulin pump electronics 524 operable to control the insulin pump drive 520, and battery compartment 526 having a battery compartment interior volume 527. A data acquisition device can be placed in the battery compartment interior volume 527 and the insulin pump 500 worn by the patient. Environmental data recovered from the data acquisition device to analyze environmental conditions to which the insulin pump has been exposed.

Those skilled in the art will further appreciate that the insulin pump data acquisition device described herein can also be used for data acquisition in other medical devices, with the casing of the particular medical device of interest taking the place of the insulin pump casing. The data acquisition device for use with an apparatus having a battery compartment can be used with any device having a battery compartment. Exemplary medical devices include diabetes remote pump and glucose monitoring systems (e.g., Medtronic MySentry™ remote glucose monitors, OmniPod® insulin management system Personal Diabetes Managers (PDM), blood glucose meters), cardiac Holter monitoring devices (e.g., GE Healthcare MARS® Ambulatory ECG Holter monitoring system and recorders), or the like.

FIGS. 5A-5L, in which like elements share like reference numbers, illustrate one embodiment of an insulin pump data acquisition device made in accordance with the invention. The insulin pump data acquisition device can acquire and store environmental data for an insulin device under real-world conditions. In this embodiment, the insulin pump data acquisition device includes insulin pump data acquisition device components within an interior volume and can removably secure an insulin pump within an exterior volume.

Figure 5A:
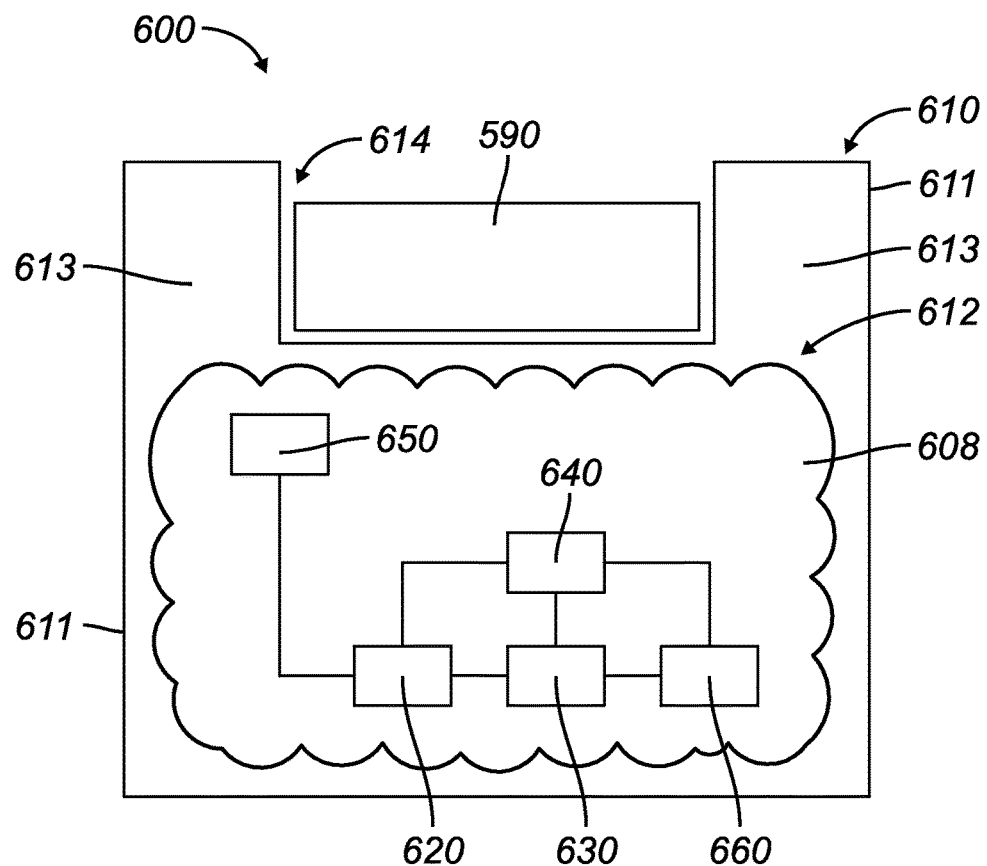
FIG. 5A is a schematic diagram of one embodiment of an insulin pump data acquisition device made in accordance with the invention.

FIG. 5A is a schematic diagram of an insulin pump data acquisition device made in accordance with the invention.

The insulin pump data acquisition device 600 for use with an insulin pump 590 includes a holster 610 having at least one wall 611 defining an interior volume 612 and an exterior volume 614, the exterior volume 614 being sized to removably secure the insulin pump 590; an environmental sensor 620 operable to generate environmental data in response to environmental conditions; memory 630 operably connected to the environmental sensor 620, the memory 630 being operable to store the environmental data; a controller 640 operably connected to the environmental sensor 620 and the memory 630, the controller 640 being operable to control reading of the environmental data from the environmental sensor 620 and writing of the environmental data to the memory 630; and a battery 650 operably connected to power the environmental sensor 620, the memory 630, and the controller 640. The insulin pump data acquisition device components 608, including the environmental sensor 620, the memory 630, the controller 640, and the battery 650, are disposed within the interior volume 612 of the holster 610. The insulin pump 590 can be disposed within the exterior volume 614. The insulin pump data acquisition device 600 can also include an optional input/output feature 660 to transfer programming instructions into and environmental data out of the insulin pump data acquisition device 600. The insulin pump 590 can be any prototype or production version of an insulin pump.

The holster 610 can be any casing or shell having one or more walls 611 to form the interior volume 612 and the exterior volume 614. The interior volume 612 can be a closed volume or can be an open volume with ports (not shown) through the wall 611 allowing the environmental sensor 620 to more rapidly detect environmental conditions around the holster 610 and the associated insulin pump 590. The exterior volume 614 can be a closed volume around the insulin pump 590 or can be an open volume which allows the insulin pump 590 to be slid into the exterior volume 614 for easy placement or removal. In one embodiment, the walls 611 can form wings 613 which extend the interior volume 612 around the insulin pump 590. One or more environmental sensors can be positioned within the interior volume 612 of the wings 613 near the side of the insulin pump 590. In one example, the walls 611 of the wings 613 include ports (not shown) through the wall 611 allowing an environmental sensor 620 positioned within the interior volume 612 of the wings 613 to more rapidly detect environmental conditions around the holster 610 and the associated insulin pump 590. Exemplary environmental sensors which can provide faster response from optimal placement include temperature sensors, humidity sensors, pressure sensors, ultraviolet sensors, electromagnetic sensors, and the like. The holster 610 can be molded, 3-D printed, or manufactured by any other method from plastic or other materials as desired to generate a particular shape.

The environmental sensor 620 can be any sensor operable to generate environmental data in response to environmental conditions. The environmental sensor 620 can be sensitive to conditions around or forces acting on the insulin pump data acquisition device 600. Exemplary environmental sensors include single axis accelerometers, multi-axis accelerometers, temperature sensors, humidity sensors, pressure sensors, ultraviolet sensors, electromagnetic sensors, and the like. The insulin pump data acquisition device 600 can include one or more environmental sensors as desired for a particular application.

The memory 630 is operably connected to the environmental sensor 620 to store the environmental data received from the environmental sensor 620. The memory 630 can store the environmental data over a period of time until the user desires to read and make use of the stored environmental data. In one example, the memory 630 is nonvolatile memory, such as flash memory or the like, in a compact format such as microSD or the like. The storage capacity of the memory 630 can be selected to store the desired number of data points of environmental data. The environmental data can be stored in any format desired, such as comma separated value format or the like. The stored data can also include a real time clock for each data point provided by the controller 640 and used to determine the time when each data point of environmental data was taken.

The controller 640 is operably connected to the environmental sensor 620 and the memory 630, to control reading of the environmental data from the environmental sensor 620 and writing of the environmental data to the memory 630. In one embodiment, the controller 640 is a microcontroller, i.e., a small computer on a single integrated circuit containing a processor core, memory, and programmable input/output peripherals. In one embodiment, the controller 640 is reprogrammable to set the frequency of the reading of the environmental data to the frequency desired for a particular application. When the insulin pump data acquisition device 600 includes more than one environmental sensor, the insulin pump data acquisition device 600 can also include one or more controllers dedicated to the operation of each environmental sensor. In one embodiment, the controller 640 is a dual-core logger which includes a first controller and a second controller, with the first controller managing acquisition of environmental data from the environmental sensor 610 and the second controller managing storage of the environmental data in the memory 630. The use of two controllers can reduce error in the timing of the environmental data which can arise from digital signal processing and which can result in inaccurate results, particularly for high frequency events such as higher frequency accelerometer events.

The battery 650 is operably connected to power the environmental sensor 620, the memory 630, and the controller 640. The battery 650 can be any battery with sufficient voltage and capacity desired for a particular application. Exemplary battery types include nickel-cadmium (NiCd), nickel-zinc (NiZn), nickel metal hydride (NiMH), lithium-ion (Li-ion), lithium polymer, alkaline, silver-oxide, and the like. In one embodiment, the battery 650 can be rechargeable. In one embodiment, the battery 650 is a single use AAA alkaline battery with a 5 V step up voltage regulator.

In another embodiment, the battery 650 is a 3 V rechargeable lithium ion coin cell battery with a 5 V step up voltage regulator.

The insulin pump data acquisition device 600 can also include an optional input/output element 660 to transfer programming instructions into and environmental data out of the insulin pump data acquisition device 600. In one embodiment, the input/output element 660 is a USB plug. In another embodiment, the input/output element is a radio frequency receiver/transmitter.

Figure 5G:
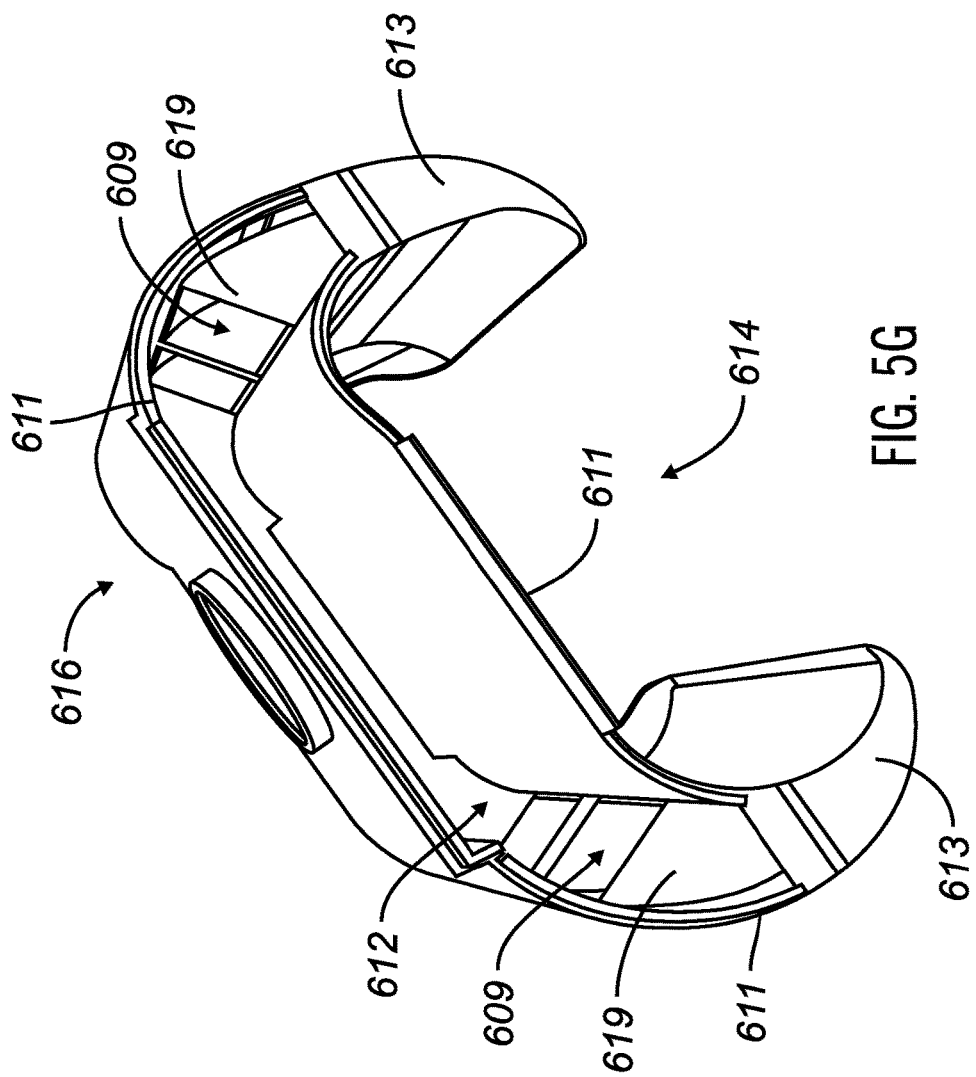

FIGS. 5B-5F are schematic diagrams of the holster of an insulin pump data acquisition device as illustrated in FIG. 5A, FIGS. 5B-5F being schematic diagrams of the holster and FIG. 5G being a schematic diagram of the interior volume.

FIGS. 5B-5F are perspective, side, front, back, and top views for one embodiment of the holster of an insulin pump data acquisition device as illustrated in FIG. 5A. Referring to FIGS. 5B-5F, the holster 610 in this embodiment includes a head portion 615 and a base portion 616, which are fixedly or removably attached to each other to form the holster 610. The external volume 614 is defined by the walls of the wings 613, external volume end 618, and back wall 617. The external volume 614 is sized to receive an infusion pump (not shown), which in this embodiment is slideably receivable in the external volume 614. The holster 610 can include fittings to allow the holster 610 to be attached to a belt or other article of clothing.

FIG. 5G is a schematic diagram of the interior volume of the holster of an insulin pump data acquisition device as illustrated in FIG. 5A. Referring to FIG. 5G, the walls 611 of the base portion 616 include partitions 619 within the interior volume 612 which further divide the interior volume 612 into partition volumes 609. The insulin pump data acquisition device components can be disposed anywhere within the interior volume 612, including the partition volumes 609. In one embodiment, environmental sensors (not shown) can be disposed within the partition volumes 609. In one embodiment, the environmental sensors (not shown) can be affixed to the walls 611. The walls 611 of the wings 613 can optionally include one or more ports (not shown) adjacent to the environmental sensor and in communication with the partition volumes 609 to allow the environmental sensor disposed within the partition volume 609 to more rapidly detect environmental conditions around the holster and the associated insulin pump. In one embodiment, the one or more ports can include a transparent window to allow the passage of light, ultraviolet radiation, or other electromagnetic radiation.

Figure 5H:
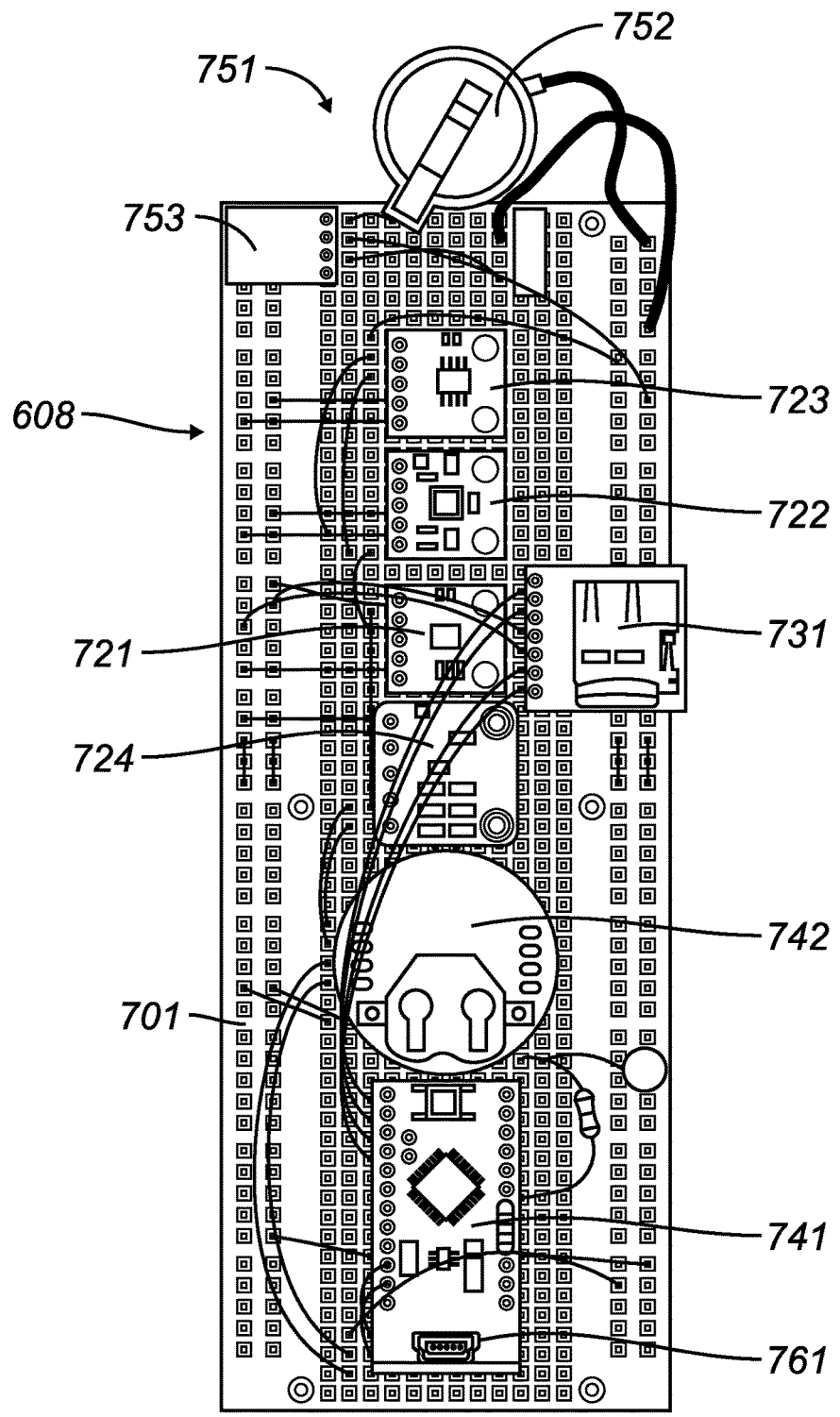
Figure 5I:
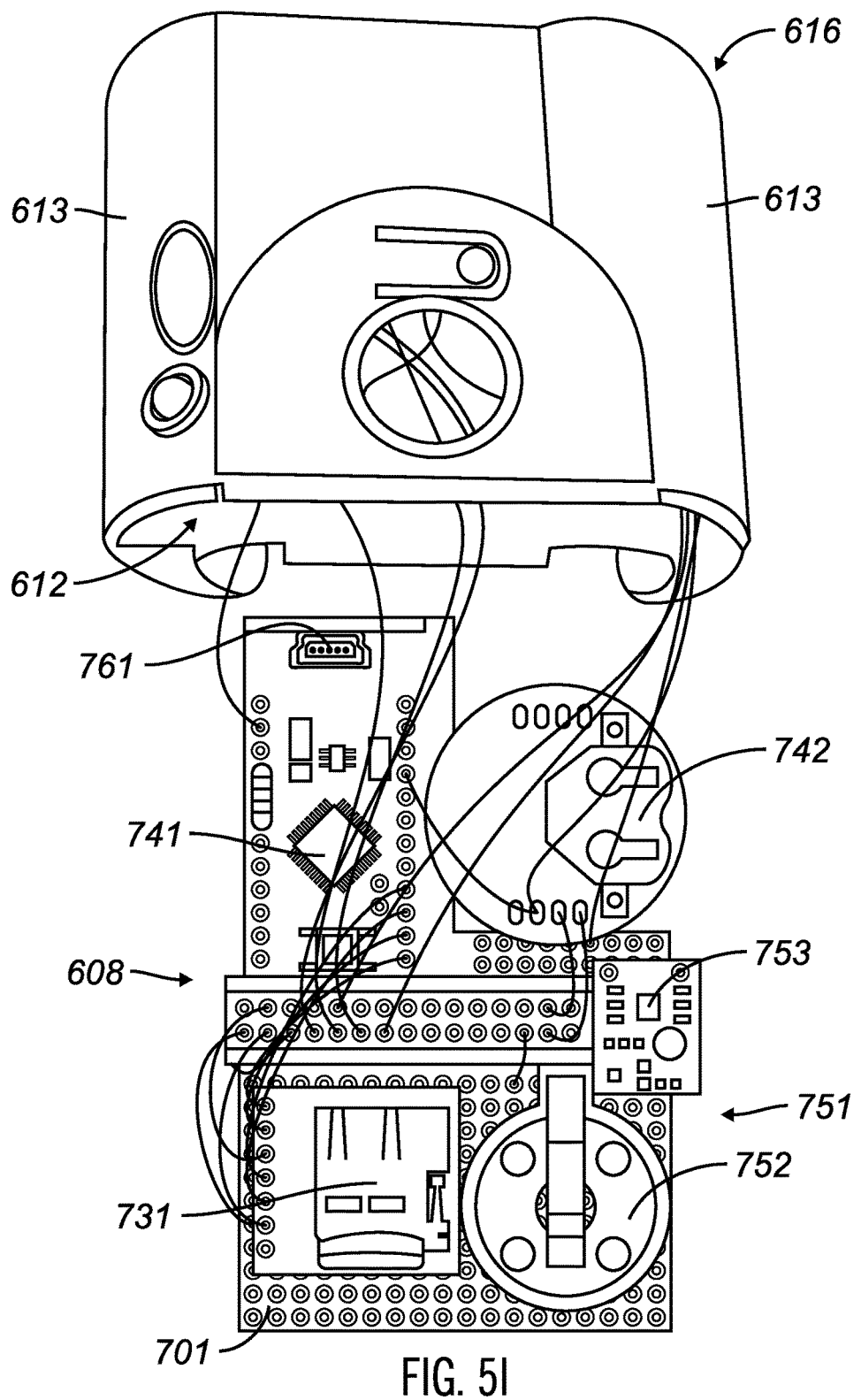
Figure 5J:
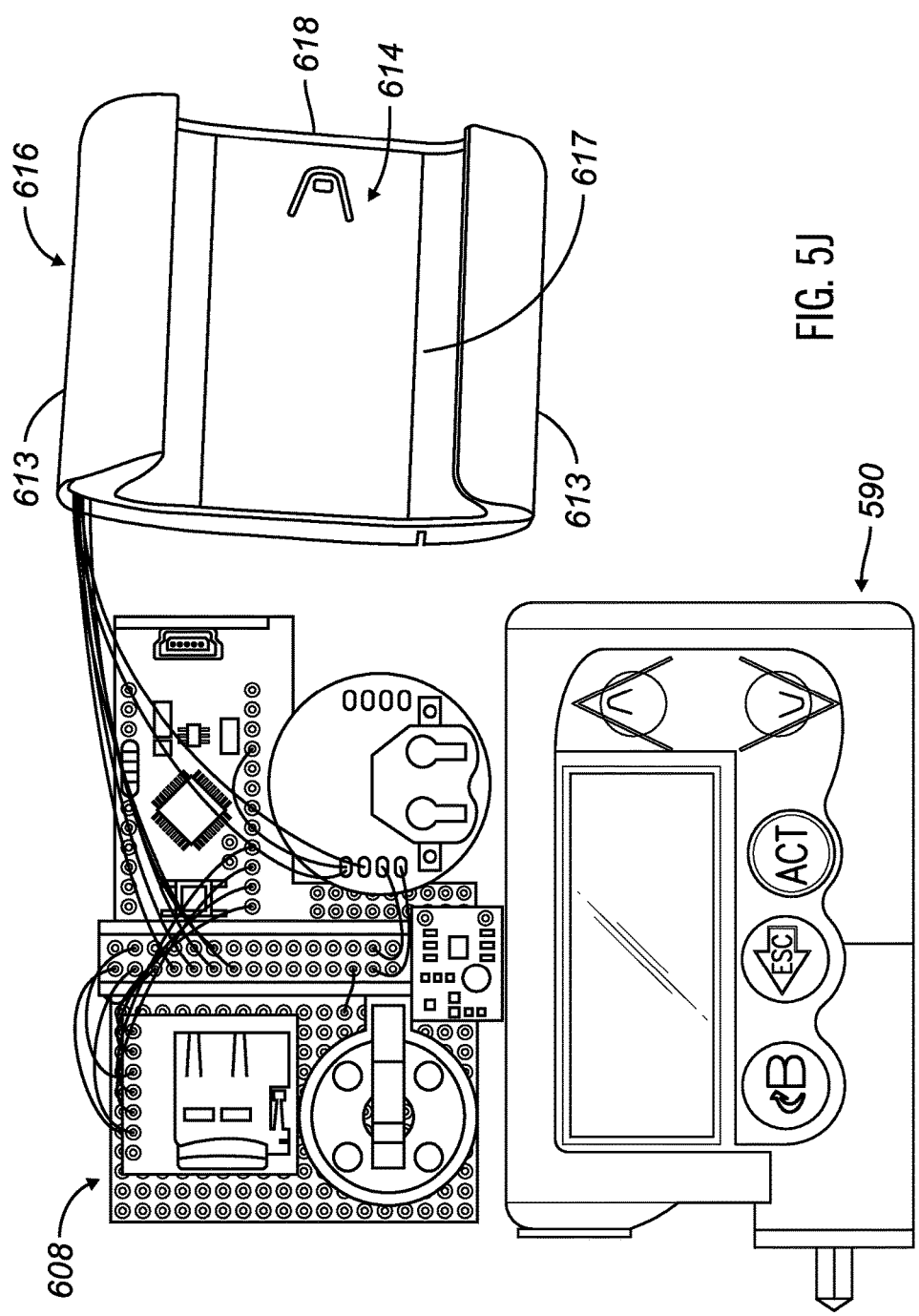

FIGS. 5H-5L are photographs of the embodiment of an insulin pump data acquisition device as illustrated in FIG. 5A, FIG. 5H being a breadboard of the circuit for the insulin pump data acquisition device, FIGS. 5I & 5J being partially assembled views of the insulin pump data acquisition device, and FIGS. 5K & 5L being assembled views of the insulin pump data acquisition device.

FIG. 5H is a breadboard of the circuit for the insulin pump data acquisition device. The insulin pump data acquisition device components 608 on the circuit board 701 includes an acceleration sensor 721, a pressure sensor 722, a temperature/humidity sensor 723, and an ultraviolet sensor 724; removable microSD memory 731; controller 741 including input/output feature 761; real time clock 742; and battery 751 including rechargeable coin cell battery 752 and step up voltage regulator 753. The acceleration sensor 721 in this example is a three axis accelerometer and is operable to generate acceleration data in response to acceleration conditions on the insulin pump data acquisition device. The pressure sensor 722 in this example is operable to generate pressure data in response to pressure conditions on the insulin pump data acquisition device. The temperature/humidity sensor 723 in this example is operable to generate temperature data and humidity data in response to data and humidity conditions, respectively, on the insulin pump data acquisition device. The ultraviolet sensor 724 is operable to generate ultraviolet data in response to ultraviolet conditions on the insulin pump data acquisition device.

The controller 741 is operable to control reading of the environmental data from the acceleration sensor 721, pressure sensor 722, temperature/humidity sensor 723, and ultraviolet sensor 724, and to control writing of the environmental data to the removable microSD memory 731. The input/output feature 761 is operable to upload/download software and/or data to or from the controller 741. The real time clock 742, powered by a dedicated battery (coin cell attached to the real time clock 742) to maintain continuous time when the insulin pump data acquisition device is powered down, generates a timestamp stored in association with the environmental data on the removable microSD memory 731 by the controller 741. The timestamp makes it possible to align usage conditions with pump activity. In applying the timestamps, the environmental data includes a number of records generated over time, the insulin pump data acquisition device further includes the real time clock 742 operably connected to provide timestamps to the controller 741, and the controller 741 is further operable to assign one of the timestamps to each of the number of records.

The removable microSD memory 731 is operable to store the environmental data, i.e., the acceleration data, pressure data, temperature data, humidity data, and ultraviolet data. The removable microSD memory 731 is operable to store the environmental data. The environmental data can be transferred to an external device by removal of the microSD card from the removable microSD memory 731 and transfer of the microSD card to the external device. The battery 751 including the rechargeable coin cell battery 752 and step up voltage regulator 753 powers the circuit board 701. In another embodiment, the battery 751 can be a single use AAA alkaline battery.

Those skilled in the art will appreciate that the environmental sensors can be selected as desired for a particular application. In this example, the acceleration sensor 721 is a MMA8452Q Low g, 12-bit Digital Accelerometer manufactured by Freescale Semiconductor, Inc., of Austin, Tex. The acceleration sensor 721 is a smart low-power, three-axis, capacitive MEMS accelerometer with 12 bits of resolution with user-selectable full scale ranges of ±2 g/±4 g/±8 g. In this example, the pressure sensor 722 is a BMP180 digital pressure sensor manufactured by Bosch Sensortec GMBH of Reutlingen, Germany. The pressure sensor 722 is a high-precision, low-power digital barometer and has a pressure sensing range of 300-1100 hPa with a typical absolute accuracy of +2/−4 hPa between 0 and 65 degrees Celsius. In this example, the temperature/humidity sensor 723 is a HIH-6130 Digital Humidity/Temperature Sensor manufactured by Honeywell Sensing and Control of Morristown, N.J. The temperature/humidity sensor 723 is a digital output-type relative humidity (RH) and temperature sensor combined, with a compensated temperature range from 5 to 50 degrees Celsius, a temperature accuracy of +/−1 degrees Celsius, and a compensated humidity range from 10% to 90% relative humidity and an accuracy of +/−4% relative humidity. In this example, the ultraviolet sensor 724 is a Si1145 Proximity/UV/Ambient Light Sensor IC manufactured by Silicon Laboratories of Austin, Tex. The ultraviolet sensor 724 is a low-power, reflectance-based, infrared proximity, ultraviolet (UV) index, and ambient light sensor, which calculates the ultraviolet (UV) index indicative of the strength of ultraviolet radiation from the sun.

Those skilled in the art will appreciate that any number and any type of environmental sensors can be selected as desired for a particular application. In one embodiment, one of the environmental sensors is an electromagnetic sensor operable to generate electromagnetic data in response to electromagnetic conditions on the insulin pump data acquisition device. In one embodiment, the electromagnetic sensor is a magnetometer operable to determine the strength and direction of magnetic fields around the insulin pump data acquisition device, both from the insulin pump itself and from the environment. In one example, the electromagnetic sensor is a HMC5883L 3-Axis Compass IC low-field magnetic sensor manufactured by Honeywell of Plymouth, Minn., with a field range of ±8 Gauss.

In this example, the controller 741 is a Arduino Pro Mini 328 single-board microcontroller, manufactured by SparkFun Electronics of Niwot, Colo. The controller 741 uses a ATmega328 microcontroller from Atmel Corporation of San Jose, Calif. The programming for the controller 741 is written in C or C++ and developed on the Arduino integrated development environment (IDE), which is a cross-platform application written in Java. In one embodiment, the programming optimizes battery life. In another embodiment, the programming optimizes environmental sensor sampling rate. In yet another embodiment, the programming balances battery life with environmental sensor sampling rate. In one embodiment when the insulin pump data acquisition device includes a number of environmental sensors, the programming can collect environmental data from preselected environmental sensors of interest for a particular application, rather than collect environmental data from all the environmental sensors. In another embodiment, the programming can collect environmental data from all of the environmental sensors. In this example, the controller 741 is operably connected to an input/output feature 761 operable to upload software and/or data to the controller 741. In one embodiment, the controller 640 is a dual-core logger which includes a first controller and a second controller, with the first controller managing acquisition of environmental data from the environmental sensor 610 and the second controller managing storage of the environmental data in the memory 630. In this dual-logger example, both the first controller and second controller are Arduino Pro Mini 328 microcontrollers, which allows for more reliable logging at sample rates of 100 times faster than a single-core logger.

In this example, the real time clock 742 is a ChronoDot RTC real time clock module, available from manufactured by SparkFun Electronics of Niwot, Colo., and based on the Maxim DS3231SN temperature compensated RTC manufactured by Maxim Integrated of San Jose, Calif. The real time clock 742 is accurate to ±2 ppm when operated between 0 and 40 degrees Celsius. The real time clock 742 can be powered by a dedicated battery to maintain continuous time when the insulin pump data acquisition device is powered down.

In this example, the battery 751 includes the coin cell battery 752, such as a 3.0V CR2032 lithium coin cell battery, and step up voltage regulator 753 powers the circuit board 701, such as a Pololu 5V Step-Up Voltage Regulator U1V11F5 available from Pololu Corporation of Las Vegas, Nev. In other embodiments, the battery 751 can be a single use AAA alkaline battery, such as a 1.5V AAA alkaline battery, a 3.7V lithium-ion battery, or a rechargeable coin cell (such as Panasonic VL3032) with a step up voltage regulator, such as a Pololu 5V Step-Up Voltage Regulator U1V11F5 available from Pololu Corporation of Las Vegas, Nev. Such batteries are operable to power the insulin pump data acquisition device approximately 22 to 99 hours until depletion, depending on battery chemistry and size.

FIGS. 5I & 5J, in which like elements share like reference numbers with FIG. 5H, are partially assembled views of the insulin pump data acquisition device. Referring to FIG. 5I, the environmental sensors (not shown), including the acceleration sensor, pressure sensor, temperature/humidity sensor, and ultraviolet sensor, have been installed within the partition volumes of the interior volume 612 in the wings 613. In one example, the acceleration sensor and ultraviolet sensor are installed in one of the wings 613 and the pressure sensor and temperature/humidity sensor are installed in the other of the wings 613. The base portion 616 of the holster is shown in a back view. Referring to FIG. 5J, the base portion 616 of the holster is shown in a front view next to the insulin pump data acquisition device components 608 and insulin pump 590, which in this example is a Medtronic MiniMed Paradigm Revel insulin pump. The insulin pump data acquisition device components 608 are aligned for placement within the interior volume 612 of the base portion 616 of the holster.

FIGS. 5K & 5L are assembled views of the insulin pump data acquisition device. The insulin pump 590 is slideably positioned in the exterior volume of the insulin pump data acquisition device 600. The head portion 615 and base portion 616 are attached to each other to form the holster 610. The insulin pump data acquisition device components 608 are disposed within the interior volume of the holster 610. The wall of the holster 610 can optionally include ports and/or openings to allow access to the insulin pump data acquisition device components for environmental data measurement, power input, data output (electronically or microSD card retrieval), programming input, and the like. Those skilled in the art will appreciate that the insulin pump data acquisition device components 608 can be secured within the holster 610 with adhesive, mechanical fittings, or the like, as desired for a particular application.

In use, the insulin pump data acquisition device 600 can be worn by the patient with the insulin pump 590 in the usual manner and environmental data recovered from the insulin pump data acquisition device 600 to analyze environmental conditions to which the insulin pump 590 has been exposed. In this example, the holster 610 includes a clip 602 as a fitting to allow the holster 610 to be attached to a belt or other article of clothing.

It is important to note that FIGS. 1-5 illustrate specific applications and embodiments of the invention, and are not intended to limit the scope of the present disclosure or claims to that which is presented therein. Upon reading the specification and reviewing the drawings hereof, it will become immediately obvious to those skilled in the art that myriad other embodiments of the invention are possible, and that such embodiments are contemplated and fall within the scope of the presently claimed invention.

Those skilled in the art will appreciate that the elements described in conjunction with FIG. 5 can be applied to the embodiments described in FIGS. 1-4 and vice versa. In one example, the embodiments described in FIGS. 1-4 can include an environmental sensor such as a single axis accelerometer, a multi-axis accelerometer, a temperature sensor, a humidity sensor, a pressure sensor, an ultraviolet sensor, an electromagnetic sensor, or the like. In another example for the embodiments described in FIGS. 1-4, the environmental data can include a number of records generated over time, the insulin pump data acquisition device further including a real time clock operably connected to provide timestamps to the controller, the controller being further operable to assign one of the timestamps to each of the number of records. In yet another example for the embodiments described in FIGS. 1-4, the controller includes a first controller and a second controller, the first controller being operable to control the reading of the environmental data from the environmental sensor and the second controller being operable to control the writing of the environmental data to the memory.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. An insulin pump data acquisition device for use with an insulin pump, the data acquisition device comprising:
   a holster having a wall defining an interior volume and an exterior volume, the exterior volume being sized to removably secure the insulin pump;
   an environmental sensor operable to generate environmental data in response to environmental conditions;
   memory operably connected to the environmental sensor, the memory being operable to store the environmental data;
   a controller operably connected to the environmental sensor and the memory, the controller being operable to control reading of the environmental data from the environmental sensor and writing of the environmental data to the memory;
   a battery operably connected to power the environmental sensor, the memory, and the controller; and
   a real time clock operably connected to provide timestamps to the controller,
   wherein the environmental sensor, the memory, the controller, and the battery are disposed within the interior volume, and
   wherein the environmental data includes a plurality of records generated over time, the controller being further operable to assign one of the timestamps to each of the plurality of records.

2. The insulin pump data acquisition device of claim 1 wherein the environmental sensor is selected from the group consisting of a single axis accelerometer, a multi-axis accelerometer, a temperature sensor, a humidity sensor, a pressure sensor, an ultraviolet sensor, and an electromagnetic sensor.

3. The insulin pump data acquisition device of claim 1 wherein the controller comprises a first controller and a second controller, the first controller being operable to control the reading of the environmental data from the environmental sensor and the second controller being operable to control the writing of the environmental data to the memory.

4. The insulin pump data acquisition device of claim 1 wherein the memory is removable microSD memory.

5. The insulin pump data acquisition device of claim 1 wherein the wall further defines a port through the wall adjacent to the environmental sensor.

6. The insulin pump data acquisition device of claim 1 further comprising an input/output feature operably connected to program the controller.

7. The insulin pump data acquisition device of claim 1 further comprising an input/output feature operably connected to recharge the battery.

8. The insulin pump data acquisition device of claim 1 wherein the environmental sensor is affixed to the wall.

9. An insulin pump data acquisition system comprising:
   an insulin pump;
   a holster having walls defining an interior volume and an exterior volume, the exterior volume being sized to removably secure the insulin pump;
   an environmental sensor operable to generate environmental data in response to environmental conditions;
   memory operably connected to the environmental sensor, the memory being operable to store the environmental data;
   a controller operably connected to the environmental sensor and the memory, the controller being operable to control reading of the environmental data from the environmental sensor and writing of the environmental data to the memory;
   a battery operably connected to power the environmental sensor, the memory, and the controller; and
   a real time clock operably connected to provide timestamps to the controller,
   wherein the environmental sensor, the memory, the controller, and the battery are disposed within the interior volume, and
   wherein the environmental data includes a plurality of records generated over time, the controller being further operable to assign one of the timestamps to each of the plurality of records.

10. The insulin pump data acquisition system of claim 9 wherein the environmental sensor is selected from the group consisting of a single axis accelerometer, a multi-axis accelerometer, a temperature sensor, a humidity sensor, a pressure sensor, an ultraviolet sensor, and an electromagnetic sensor.

11. The insulin pump data acquisition system of claim 9 wherein the controller comprises a first controller and a second controller, the first controller being operable to control the reading of the environmental data from the environmental sensor and the second controller being operable to control the writing of the environmental data to the memory.

12. The insulin pump data acquisition system of claim 9 wherein the memory is removable microSD memory.

13. The insulin pump data acquisition device of claim 9 wherein the walls further define a port through at least one of the walls adjacent to the environmental sensor.

14. The insulin pump data acquisition device of claim 9 further comprising an input/output feature operably connected to program the controller.

15. The insulin pump data acquisition device of claim 9 further comprising an input/output feature operably connected to recharge the battery.

16. An insulin pump data acquisition device comprising:
   an insulin pump casing having an interior volume;
   an environmental sensor operable to generate environmental data in response to environmental conditions;
   memory operably connected to the environmental sensor, the memory being operable to store the environmental data;
   a controller operably connected to the environmental sensor and the memory, the controller being operable to control reading of the environmental data from the environmental sensor and writing of the environmental a battery operably connected to power the environmental sensor, the memory, and the controller; and a real time clock operably connected to provide timestamps to the controller, wherein the environmental sensor, the memory, the controller, and the battery are disposed within the interior volume, and the environmental sensor is selected from the group consisting of a single axis accelerometer, a multi-axis accelerometer, a temperature sensor, a humidity sensor, a pressure sensor, an ultraviolet sensor, and an electromagnetic sensor, and wherein the environmental data includes a plurality of records generated over time, the controller being further operable to assign one of the timestamps to each of the plurality of records.

17. The insulin pump data acquisition device of claim 16 wherein the controller comprises a first controller and a second controller, the first controller being operable to control the reading of the environmental data from the environmental sensor and the second controller being operable to control the writing of the environmental data to the memory.

\* \* \* \* \*